(12) United States Patent
Sarnow et al.

(10) Patent No.: US 11,627,934 B2
(45) Date of Patent: *Apr. 18, 2023

(54) NON-INVASIVE DETERMINATION OF PENNATION ANGLE AND/OR FASCICLE LENGTH

(71) Applicant: MuscleSound, Inc., Glendale, CO (US)

(72) Inventors: Pierre Sarnow, Littleton, CO (US); Stephen S. Kurtz, Englewood, CO (US); Andrew D. Jackson, Denver, CO (US); Wayne Phillips, Gilbert, AZ (US)

(73) Assignee: MUSCLESOUND, LLC, Glendale, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/374,779

(22) Filed: Jul. 13, 2021

(65) Prior Publication Data
US 2021/0338196 A1 Nov. 4, 2021

Related U.S. Application Data

(63) Continuation of application No. 15/794,212, filed on Oct. 26, 2017, now Pat. No. 11,096,658.

(Continued)

(51) Int. Cl.
*A61B 8/08* (2006.01)
*A61B 8/00* (2006.01)
*A61B 5/00* (2006.01)

(52) U.S. Cl.
CPC .......... *A61B 8/0858* (2013.01); *A61B 8/4227* (2013.01); *A61B 8/5223* (2013.01);
(Continued)

(58) Field of Classification Search
CPC ... A61B 5/0013; A61B 5/4519; A61B 5/4523; A61B 5/681; A61B 8/0858;
(Continued)

(56) References Cited

U.S. PATENT DOCUMENTS 4,831,527 A 5/1989 Clark
4,876,733 A 10/1989 Lavin
(Continued)

FOREIGN PATENT DOCUMENTS

KR 20130006011 1/2013
WO WO 14/115056 7/2014

OTHER PUBLICATIONS

Zhou, "Dynamic measurement of pennation angle of gastrocnemius muscles during contractions based on ultrasound imaging", 2012 (Year: 2012).*

(Continued)

*Primary Examiner* — Katherine L Fernandez
*Assistant Examiner* — Brooke Lyn Klein
(74) *Attorney, Agent, or Firm* — Brownstein Hyatt Farber Schreck, LLP

(57) ABSTRACT

Provided is a non-invasive system and method of determining pennation angle and/or fascicle length based on image processing. An ultrasound scan image is processed to facilitate distinguishing of muscle fiber and tendon. The processed ultrasound scan image is then analyzed. The pennation angle and/or fascicle length is determined based on the analysis. An example method includes receiving an ultrasound scan image of at least a portion of a skin layer as disposed above one or more additional tissue layers, the image provided by a plurality of pixels. The method continues by introducing noise into the pixels of the image and thresholding the pixels of the image to provide a binary image having a plurality of structural elements of different sizes. The method continues with morphing the structural elements of the binary image to remove small structural elements and connect large structural elements. With this resulting image, the method distinguishes muscle fiber and tendon from remaining elements and determines the penna- (Continued)

tion angle and/or the fascicle length from the muscle fiber and the tendon. Associated apparatuses and computer program products are also disclosed.

20 Claims, 27 Drawing Sheets

Related U.S. Application Data

(60) Provisional application No. 62/453,833, filed on Feb. 2, 2017.

(52) U.S. Cl.
CPC .......... *A61B 5/0013* (2013.01); *A61B 5/4519* (2013.01); *A61B 5/4523* (2013.01); *A61B 5/681* (2013.01); *A61B 8/4461* (2013.01); *A61B 8/4483* (2013.01)

(58) Field of Classification Search
CPC ... A61B 8/4227; A61B 8/4461; A61B 8/4483; A61B 8/5223; G16H 50/30
See application file for complete search history.

(56) References Cited

U.S. PATENT DOCUMENTS

| | | | |
|---|---|---|---|
| 5,208,747 A | 5/1993 | Wilson et al. | |
| 5,670,135 A | 9/1997 | Schroder | |
| 5,941,825 A | 8/1999 | Lang et al. | |
| 6,542,250 B1 | 2/2003 | Weber et al. | |
| 6,656,121 B2 | 12/2003 | Jeong et al. | |
| 6,705,994 B2 | 3/2004 | Vortman et al. | |
| 6,891,961 B2 | 5/2005 | Eger et al. | |
| 7,658,714 B2 | 2/2010 | Leibig et al. | |
| 7,664,298 B2 | 2/2010 | Lang et al. | |
| 7,683,617 B2 | 3/2010 | Van Zijl et al. | |
| 7,809,153 B2 | 10/2010 | Bravomalo | |
| 7,918,794 B2 | 4/2011 | Pineau et al. | |
| 8,135,179 B2 | 3/2012 | Wilson et al. | |
| 8,351,655 B2 | 1/2013 | Hwang | |
| 8,512,247 B2 | 8/2013 | Hill | |
| 8,517,942 B2 | 8/2013 | Hill | |
| 8,562,529 B2 | 10/2013 | Hill | |
| 8,715,187 B2 | 5/2014 | Davis et al. | |
| 8,811,745 B2 | 8/2014 | Farsiu et al. | |
| 9,364,179 B2 | 6/2016 | Hill | |
| 9,579,079 B2 | 2/2017 | Jeanne et al. | |
| 9,642,593 B2 | 5/2017 | Sarnow et al. | |
| 9,996,926 B2 | 6/2018 | Leinhard et al. | |
| 10,028,700 B2 | 7/2018 | Sarnow et al. | |
| 10,157,465 B2 | 12/2018 | Sugiyama et al. | |
| 10,463,346 B2 | 11/2019 | Hill et al. | |
| 10,548,528 B2 | 2/2020 | Appleby | |
| 11,013,490 B2 | 5/2021 | Sarnow et al. | |
| 2003/0018257 A1 | 1/2003 | Hsu et al. | |
| 2006/0184024 A1 | 8/2006 | Da Silva et al. | |
| 2007/0016061 A1 | 1/2007 | Da Silva et al. | |
| 2009/0012406 A1* | 1/2009 | Llewellyn ............ | A61B 5/0044 600/478 |
| 2009/0264756 A1 | 10/2009 | Da Silva et al. | |
| 2009/0270728 A1 | 10/2009 | Da Silva et al. | |
| 2010/0036246 A1 | 2/2010 | Kushculey et al. | |
| 2012/0116223 A1 | 5/2012 | Da Silva et al. | |
| 2012/0165703 A1 | 6/2012 | Bottum | |
| 2012/0254749 A1 | 10/2012 | Downs, III et al. | |
| 2013/0123629 A1 | 5/2013 | Rosenberg et al. | |
| 2015/0045690 A1* | 2/2015 | Uchiyama ............ | A61B 5/742 600/547 |
| 2015/0374343 A1 | 12/2015 | Shan et al. | |
| 2018/0146947 A1 | 5/2018 | Sarnow et al. | |
| 2018/0214118 A1 | 8/2018 | Sarnow et al. | |
| 2018/0249946 A1 | 9/2018 | Sarnow et al. | |
| 2021/0236085 A1 | 8/2021 | Sarnow et al. | |
| 2021/0378587 A1 | 8/2021 | Sarnow et al. | |
| 2021/0321979 A1 | 10/2021 | Sarnow et al. | |

OTHER PUBLICATIONS

Ramsay, Differences in plantar flexor fascicle length and pennation angle between healthy and poststroke individuals and implications for poststroke plantar flexor force contributions, 2014 (Year: 2014).*

Siping, "The correlation of muscle thickness and pennation angle assessed by ultrasound with sarcopenia in elderly Chinese community dwellers", 2019 (Year: 2019).*

Costill et al., "Muscle glycogen utilization during prolonged exercise on successive days," *Journal of Applied Physiology,* 1971, vol. 31, No. 6, pp. 834-838.

Definition of "doubling," https://www.thefreedictionary.com/doubling, retrieved on Jan. 28, 2021.

Elamaran et al., "A Case Study of Impulse Noise Reduction Using Morphological Image Processing with Structuring Elements," *Asian Journal of Scientific Research,* vol. 8, No. 3, 2015, pp. 291-303.

Fisher et al., "Spatial Filters—Gaussian Smoothing," https://homepages.inf.ed.ac.uk/rbf/HIPR2/gsmooth.htm, Apr. 24, 2020, 9 pages.

Gabriel et al., "Ultrasound of the abdomen in endurance athletes," *Eur J Appl Physiol,* 1996, vol. 73, pp. 191-193.

Jackson et al., "Practical Assessment of Body Composition," *Physicians Sports Medicine,* 1985, vol. 13, pp. 76-90.

Kadah et al., "Classification Algorithms for Quantitative Tissue Characterization of Diffuse Liver Disease from Ultrasound Imaages," *IEEE Transactions on Medical Imaging,* 1996, vol. 15, No. 4, pp. 466-478.

Koda et al., "Sonographic subcutaneous and visceral fat indices represent the distribution of body fat volume," *Abdominal Imaging,* 2007, vol. 32, pp. 387-392.

Leahy et al., "Ultrasound Measurement of Subcutaneous Adipose Tissue Thickness Accurately Predicts Total and Segmental Body Fat of Young Adults," Ultrasound in Medicine and Biology, 2012, vol. 38, No. 1, pp. 28-34.

MathWorks Announces Release 2014a of the MATLAB and Simulink Product Families, https://www.mathworks.com/company/newsroom/mathworks-announces-release-2014a-of-the-matlab-and-simulink-product-families.html, Mar. 7, 2014, 6 pages.

Nguyen et al., "Contrast-Enhanced Ultrasonography in Patients with Glycogen Storage Disease Type Ia and Adenomas," *Journal of Ultrasound Medicine,* 2009, vol. 28, pp. 497-505.

Price et al., "Effect of muscle glycogen content on exercise-induced changes in muscle T2 times," *Muscle Glycogen, Exercise, and T2 Times,* 1998, pp. 1178-1184.

Salvi, "Architectural Analysis of Musculoskeletal Ultrasound Images," Politecnico di Torino, Dec. 2014, 61 pages.

Steensberg et al., "Muscle glycogen content and glucose uptake during exercise in humans: influence of prior exercise and dietary manipulation," *Journal of Physiology,* vol. 541.1, 2002, pp. 273-281.

The University of Auckland, "Gaussian Filtering," May 25, 2010, 15 pages.

Wagner, "Ultrasound as a Tool to Assess Body Fat," *Journal of Obesity,* vol. 2013, Article ID 280713, 9 pages.

Zhou et al., "Automatic measurement of pennation angle and fascicle length of gastrocnemius muscles ultrasound imaging," Ultrasonics, vol. 57, 2015, pp. 72-83.

U.S. Appl. No. 17/234,551, filed Apr. 19, 2021, Sarnow et al.

U.S. Appl. No. 17/363,780, filed Jun. 30, 2021, Sarnow et al.

Definition of "Sleek," https://https://www.merriam-webster.com/dictionary/sleek, retrieved on Aug. 2022.

Hendrick et al., "Image and Signal Processing in Diagnostic Ultrasound Imaging" JDMS 1989 5:231-239.

* cited by examiner

NON-INVASIVE DETERMINATION OF PENNATION ANGLE AND/OR FASCICLE LENGTH

CROSS-REFERENCE TO RELATED APPLICATIONS

This application is a continuation of U.S. patent application Ser. No. 15/794,212, filed Oct. 26, 2017, which claims the benefit under 35 U.S.C. § 119(e) of U.S. Provisional Patent Application No. 62/453,833, filed on Feb. 2, 2017, the contents of which are incorporated herein by reference as if fully disclosed herein.

FIELD

The described embodiments relate generally to the field of fitness and healthcare and more specifically to non-invasive determination of pennation angle and/or fascicle length.

BACKGROUND

The human body is composed of many types of tissues, not the least of which are bone, muscle, nervous, connective, circulatory and, of course, muscle tissue. For most people, certain types of tissues within the body, such as skeletal muscle tissue, can be altered by choices in diet and exercise.

Determination of pennation angle (the angle at which muscle fibers attach to tendon) and/or fascicle length (the length of bundles of muscle fibers surrounded by connective tissue) may be useful for a variety of reasons. For example, professional athletes may use such measurements to adjust a training regimen. By way of another example, medical professionals may use such measurements for evaluating the safety of treatments for patients. In yet another example, fitness enthusiasts may use such measurements to guide a fitness regimen.

The most accurate way to determine the pennation angle and/or fascicle length is through dissection, which is simply not a feasible option for living human beings. Non-invasive methods have been developed, but are generally not accurate.

SUMMARY

The present disclosure relates to non-invasive determination of pennation angle and/or fascicle length. An ultrasound scan image is processed to facilitate distinguishing of muscle fiber and tendon. The processed ultrasound scan image is then analyzed. The pennation angle and/or fascicle length is determined based on the analysis.

In some embodiments, an electronic device that determines pennation angle includes at least one non-transitory storage medium that stores instructions and at least one processing unit. The at least one processing unit executes the instructions to receive an ultrasound scan image of at least a portion of a skin layer as disposed above one or more additional tissue layers, the ultrasound scan image provided by a plurality of pixels; introduce noise into the pixels of the ultrasound scan image; threshold the pixels of the ultrasound scan image to provide a binary image having a plurality of structural elements of different sizes; morph the structural elements of the binary image to remove small structural elements and connect large structural elements; and determine the pennation angle using the morphed binary image.

In various examples, the at least one processing unit determines the pennation angle by finding features in the morphed binary image, measuring angles of the features; and subtracting a portion of the measured angles from a reference fascia angle of a reference fascia. In some implementations of such examples, the at least one processing unit determines a top pennation angle and a bottom pennation angle. In such implementations, the at least one processing unit may determine the top pennation angle by processing a first version of the ultrasound scan image and the bottom pennation angle by processing a second version of the ultrasound scan image. The at least one processing unit may generate at least one of the first version of the ultrasound scan image by cropping the ultrasound scan image above the reference fascia or the second version of the ultrasound scan image by cropping the ultrasound scan image below the reference fascia. In some examples, the reference fascia is a fascial boundary between at least one of a rectus femoris muscle and vastus intermedius muscle or a vastus lateralis muscle and the vastus intermedius muscle.

In some examples, the at least one processing unit computes features in the morphed binary image, finds a reference fascia in the morphed binary image using the computed features, and determines a reference fascia angle for the reference fascia.

In various embodiments, a non-invasive method of determining pennation angle includes providing an ultrasound device having a movable transducer, the movable transducer operable in a high frequency range, selecting a target area of a subject, adjusting the ultrasound device for a depth of scan appropriate for the selected target area, disposing the movable transducer proximate to the subject and to the selected target area, scanning the selected target area by processing ultrasound reflection received by the movable transducer to provide at least a partial scan image of the selected target area, the partial scan image provided by a plurality of pixels, introducing noise into the pixels of the partial scan image, thresholding the pixels of the partial scan image to provide a binary image having a plurality of structural elements of different sizes, morphing the structural elements of the binary image to remove small structural elements and connect large structural elements, and determining the pennation angle by analyzing the morphed binary image.

In some examples, the method further includes reporting an indication of the pennation angle. In numerous examples, the method further includes comparing the pennation angle to at least one of a previous determination or a peer group. In various examples, the method further includes evaluating pennation angle where larger values correspond to higher force exertion ability and lower contraction speed and smaller values correspond to lower force exertion ability and higher contraction speed. In some examples, the method further includes providing output based on the pennation angle related to altering the pennation angle.

In various examples, the method further includes evaluating fitness of the subject for an activity based on the pennation angle. In some examples, determining the pennation angle is performed about contemporaneously with imaging the subject for another purpose.

In numerous embodiments, a computer program product storing instructions executable to perform a method of determining pennation angle includes a first set of instructions, stored in at least one non-transitory computer readable medium, executable by at least one processing unit to receive an ultrasound scan image of at least a portion of a skin layer as disposed above one or more additional tissue layers, the ultrasound scan image provided by a plurality of pixels; a second set of instructions, stored in the at least one non-transitory computer readable medium, executable by the at least one processing unit to introduce noise into the pixels of the ultrasound scan image; a third set of instructions, stored in the at least one non-transitory computer readable medium, executable by the at least one processing unit to threshold the pixels of the ultrasound scan image to provide a binary image having a plurality of structural elements of different sizes; a fourth set of instructions, stored in the at least one non-transitory computer readable medium, executable by the at least one processing unit to morph the structural elements of the binary image to remove small structural elements and connect large structural elements; a fifth set of instructions, stored in the at least one non-transitory computer readable medium, executable by the at least one processing unit to distinguish muscle fiber from remaining structural elements; and a sixth set of instructions, stored in the at least one non-transitory computer readable medium, executable by the at least one processing unit to determine the pennation angle from the muscle fiber.

In various examples, the computer program product further includes a seventh set of instructions, stored in the at least one non-transitory computer readable medium, executable by the at least one processing unit to determine a fascicle length from the muscle fiber. In some cases of such examples, the computer program product further includes an eighth set of instructions, stored in the at least one non-transitory computer readable medium, executable by the at least one processing unit to report an indication of the fascicle length or compare the fascicle length to a peer group. In other cases of such examples, the computer program product further includes an eighth set of instructions, stored in the at least one non-transitory computer readable medium, executable by the at least one processing unit to evaluate the fascicle length where larger values correspond to higher force exertion ability and lower contraction speed and smaller values correspond to lower force exertion ability and higher contraction speed. In yet other cases of such examples, the computer program product further includes an eighth set of instructions, stored in the at least one non-transitory computer readable medium, executable by the at least one processing unit to provide output based on the fascicle length related to altering the fascicle length. In still other cases of such examples, the computer program product further includes an eighth set of instructions, stored in the at least one non-transitory computer readable medium, executable by the at least one processing unit to evaluate fitness of a subject for an activity based on the fascicle length.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, and computer program products that embody various elements of the present disclosure. However, it should be understood that the described disclosure may be practiced in a variety of forms in addition to those described herein.

Before proceeding with the detailed description, it is to be appreciated that the present teaching is by way of example only, not by limitation. The concepts herein are not limited to use or application with a specific system or method for non-invasive determination of pennation angle and/or fascicle length. Thus, although the instrumentalities described herein are for the convenience of explanation shown and described with respect to exemplary embodiments, it will be understood and appreciated that the principles herein may be applied equally in other types of systems and methods involving the determination of pennation angle and/or fascicle length and specifically pennation angle and/or fascicle length in humans.

Figure 1:
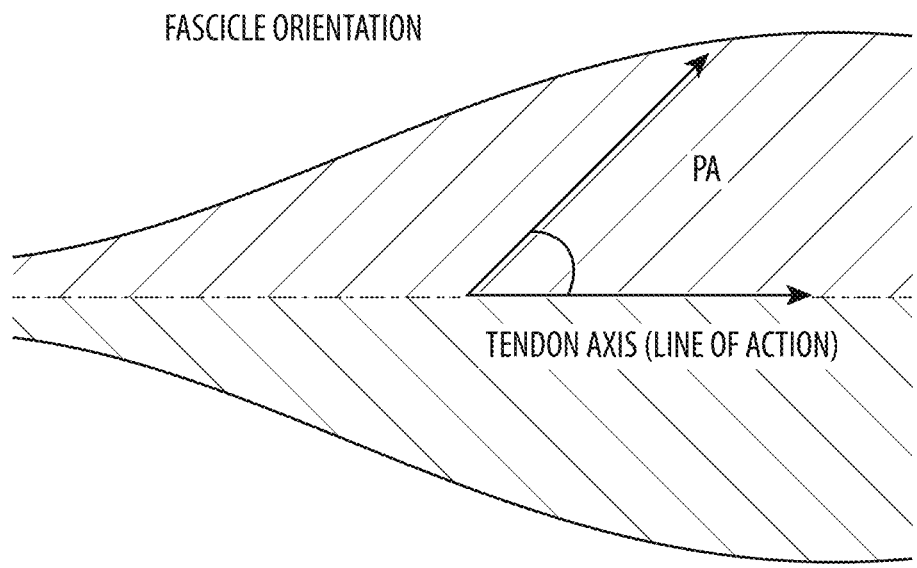
FIG. 1 depicts an example pennation angle of an example muscle tissue.

Pennation angle may be defined as the angle between a fascicles orientation and the tendon axis. Pennation angle may be an important muscle characteristic that may play a significant role in determining a fascicle's force contribution to skeletal movement. FIG. 1 depicts an example pennation angle of an example muscle tissue. Muscle thickness, fascicle length, and pennation angle have been correlated to speed, agility, strength, and intermittent sprint performance.

The "Performance and muscle architecture comparisons between starters and nonstarters in National Collegiate Athletic Association Division I women's soccer" study (available at http://www.ncbi.nlm.nih.gov/pubmed/23719503) tracked muscle thickness, pennation angle, and echo intensity of the vastus lateralis and rectus femoris in starters and nonstarters during a National Collegiate Athletic Association Division I women's soccer season. Results of this study indicate that VO2 max and muscle architecture are important characteristics of NCAA Division I women soccer players and may predict HIR (high intensity running) distance during a competitive contest. Muscle architecture in this study referred to muscle thickness and pennation angle.

The "Changes in muscle architecture and performance during a competitive season in female softball players" study (available at http://www.ncbi.nlm.nih.gov/pubmed/22847524) tested vastus lateralis thickness, pennation angle, and fascicle length pre-, mid-, and post-season in competitive female softball players. Relationships were found between muscle architecture and speed, agility, and strength parameters.

The present disclosure relates to non-invasive determination of pennation angle (the angle at which muscle fibers attach to tendon or the angle between a fascicle's orientation and the tendon axis) and/or fascicle length (the length of bundles of muscle fibers surrounded by connective tissue). An ultrasound scan image is processed to facilitate distinguishing of muscle fiber and tendon. The processed ultrasound scan image is then analyzed. The pennation angle and/or fascicle length is determined based on the analysis.

Pennation angle of muscle fiber and/or fascicle length may be an important muscle characteristic that may play a significant role in determining a fascicle's force contribution to skeletal movement. The larger the angle and/or fascicle length, the farther that the muscle may be able to move when contracting. However, the time used to contract may also be greater, reducing response time. Thus, pennation angle and/or fascicle length may be significant in correlational and/or causational relationships between muscle architecture and speed, agility, sprint performance and/or strength parameters.

Figure 2:
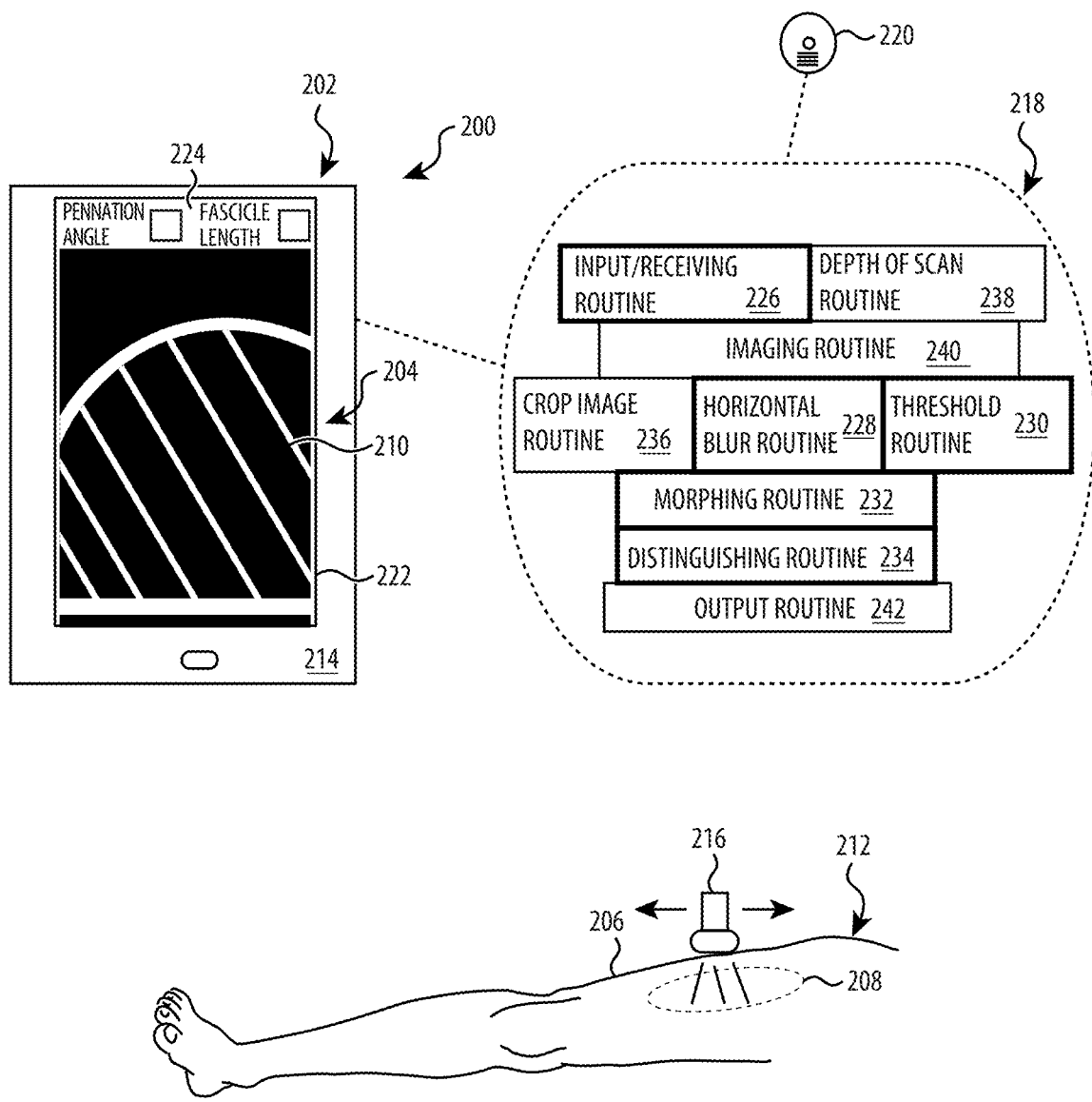
FIG. 2 depicts a high level block diagram of a system for non-invasive tissue evaluation that may be used to determine human pennation angle and/or fascicle length in accordance with at least one embodiment.

Turning to FIG. 2, presented is a high level block diagram of a system for non-invasive tissue analysis (SNTA) 200. For at least one embodiment, SNTA 200 is an evaluator 202 structured and arranged to evaluate at least one selected portion of an ultrasound scan image that has undergone image processing.

In the present example, the evaluator 202 evaluates an image 204 of at least a portion of a skin layer 206 disposed above one or more additional target tissues 208 to determine a pennation angle and/or fascicle length of muscle fiber 210. More specifically, the evaluator 202 evaluates the image 204 to determine the pennation angle and/or fascicle length of one or more muscle fibers 210 under the skin layer 206.

As used herein, the term "skin" is understood and appreciated for its normal meaning as is expected in the medical profession—namely, an ever-changing organ that contains many specialized cells organized in three generalized layers—the epidermis, the dermis and subcutaneous tissue. Of course, each of these layers may also be described as being composed of multiple layers. With respect to the present disclosure and this description, the skin layer 206 is understood and appreciated to be one or more of the layers of epidermis, dermis and subcutaneous tissue. Precise identification and distinction of these layers may not be necessary for most embodiments. Indeed, the identification of the skin layer 206 may serve generally as a point of reference in image 204. Moreover, in varying images, the skin layer 206 may be shown in an image as a portion of the subcutaneous tissue, a portion of the dermis and the subcutaneous tissue, and/or a portion of the epidermis and the dermis and the subcutaneous tissue.

As used herein the term "scan" is understood and appreciated for its normal meaning and as is expected in the medical profession—namely, "a. examination of the body or an organ or part, or a biologically active material, by means of a scanning technique such as ultrasonography—an ultrasound-based diagnostic imaging technique used for visualizing subcutaneous body structures; b. the image so obtained."

With respect to the present disclosure, and as is set forth in greater detail below and in the accompanying figures, the scan image is the element of importance. As such, as used herein, the terms "scan image," and/or "image" are understood to be synonymous. Moreover, the ultrasound transducer provides a signal that for the present disclosure is rendered as an image including a plurality of pixels. The present disclosure teaches the processing and evaluation of the resulting image, and not the processing, evaluation or transformation of the original ultrasound signal or waveform.

In at least one embodiment, SNTA 200 has a processor-enabled device such as computer 214. Computer 214 is adapted to receive the information from the ultrasound transducer 216 and provide a scan image of a portion of a skin layer 206 disposed above one or more additional target tissues 208, of the subject 212. For illustrative purposes the portion shown of the subject 212 is that of the right leg, but as will be further discussed below, SNTA 200 can be, and for at least one embodiment is, applied to multiple different locations of the subject's 212 body.

With respect to FIG. 2, SNTA 200 is at least in part conceptually illustrated in the context of an embodiment for a computer program 218. Such a computer program 218 can be provided upon a non-transitory computer readable media, such as an optical disc 220 or RAM drive that can be provided to a computer 214 to be adapted as SNTA 200. As is further shown and described in connection with FIGS. 15-21, in alternative embodiments the computer program 218 can be provided to a computer serving at least as part of an application providing platform, such as but not limited to the Apple App Store, that platform in turn operable to provide the computer program 218 to a computer 214 to be adapted as SNTA 200.

As will be discussed further below, SNTA 200 may be employed upon a computer 214 having typical components such as a processor, memory, storage devices and input and output devices. During operation, the SNTA 200 may be maintained in active memory for enhanced speed and efficiency. In addition, SNTA 200 may also be operated within a computer network and may utilize distributed resources.

In at least one embodiment, the SNTA 200 system is provided as a dedicated system to provide non-invasive tissue analysis. In at least one alternative embodiment, the SNTA 200 system is achieved by adapting an existing computer 214 which is portable, such as a smart phone (such as an iPhone® or Android®), tablet computer (such as an iPad®), an implant, a wearable device, and so on.

With respect to FIG. 2, SNTA 200 has been conceptually illustrated as a tablet computer 214, having a display 222 operable to display a visual representation of the scan image 204. The display 222 also is shown to provide an indicator 224 to inform an operator of the determined tissue analysis.

For at least one embodiment, the software may be described as including an input/receiving routine 226, a horizontal blurring or other noise introduction (such as vertical blurring, speckling, and so on) routine 228, a threshold routine 230, a morphing routine 232, and a distinguishing routine 234. As is set forth and described below, the elements of SNTA 200 may be summarized for at least one embodiment as follows.

The input/receiving routine 226 is operatively associated with an input device to receive the scan, such as a Digital Imaging and Communications in Medicine (DICOM) data file, and may also receive other information such as the subject's name, location, current state of exertion, etc. If not in image form, this received scan is provided to the operator as a scan image 204 including a plurality of pixels. The horizontal blurring routine 228 is operable to horizontally blur the pixels of the image. The thresholding routine 230 is operable to threshold each pixel to provide a binary image having a plurality of structural elements of different sizes. The morphing routine 232 is operable to morph elements of the processed image to remove small structural elements and connect large structural elements. The distinguishing routine 234 is operable to distinguish muscle fiber 210 and/or tendon from remaining structural elements and determine pennation angle and/or fascicle length.

For at least one embodiment, SNTA 200 may also include an optional cropping or crop image routine 236. As has been noted above and will be further understood and appreciated with respect to the following description, the present disclosure advantageously is distinguishing a subject's pennation angle and/or fascicle length through image processing. More specifically, image processing techniques including blurring and/or other noise introduction, thresholding, and morphing are advantageously combined so as to process a scan image 204 and provide processed image 204 in such a way as to quickly and very accurately distinguish muscle fiber 210 and/or tendon.

In this respect, for at least one embodiment, between 1/10th and 1/5th of the image is vertically cropped from one or both sides so as to leave a more central portion of the original scan image for subsequent image processing. For at least one alternative embodiment, no cropping is performed.

In addition to the core routines, an input/receiving routine 226, a horizontal blurring routine 228, a threshold routine 230, a morphing routine 232, and a distinguishing routine 234, in at least one alternative embodiment, SNTA 200 further includes an ultrasound device having a movable transducer 216 operable in a high frequency range and having an adjustable depth of scan. More specifically, the high frequency range may be between about 5 to 20 megahertz. In addition the depth of scan may be between about 1 centimeter and about 7 centimeters. For at least one embodiment, the ultrasound transducer 216 may be an existing commercially available and FDA approved ultrasound transducer 216 incorporated as part of SNTA 200 without departing from the scope of FDA approval for the operation of the ultrasound transducer 216.

For at least one embodiment of SNTA 200, the computer program 218 may additionally include a depth of scan routine 238, an imaging routine 240, and optionally an output routine 242. Moreover, the depth of scan routine 238 is operable to adjust the ultrasound device, e.g., ultrasound transducer 216, for a depth of scan appropriate for the target tissues 208. In at least one embodiment, the proper depth of scan is set based on the selection of target tissues 208 as indicated by an operator of SNTA 200.

The imaging routine 240 is operable to direct the movable transducer 216 to scan the selected target tissues 208 by processing ultrasound reflection received by the transducer 216 to provide at least a partial ultrasound scan of the selected target muscle. In at least one embodiment, the imaging routine 240 is structured and arranged to operate with a third-party ultrasound imaging software provided to the computer 214.

For at least one embodiment, the optional output routine 242 is operable to output the scan of the target tissues 208 to a storage device, or database. This output routine 242 may also be configured to provide an audible, visual or tactile output to inform the operator of SNTA 200 of the determined pennation angle and/or fascicle length of muscle fiber 210.

With respect to FIG. 2, it is understood and appreciated that the elements, e.g., input/receiving routine 226, horizontal blurring routine 228, threshold routine 230, morphing routine 232, distinguishing routine 234, crop image routine 236, depth of scan routine 238, imaging routine 240, output routine 242, ultrasound transducer 216 and computer 214 are in at least one embodiment located within a single device. In at least one alternative embodiment, these elements may be distributed over a plurality of interconnected devices. Further, although each of these elements has been shown conceptually as an element, it is understood and appreciated that in varying embodiments, each element may be further subdivided and/or integrated with one or more other elements.

Figure 3:
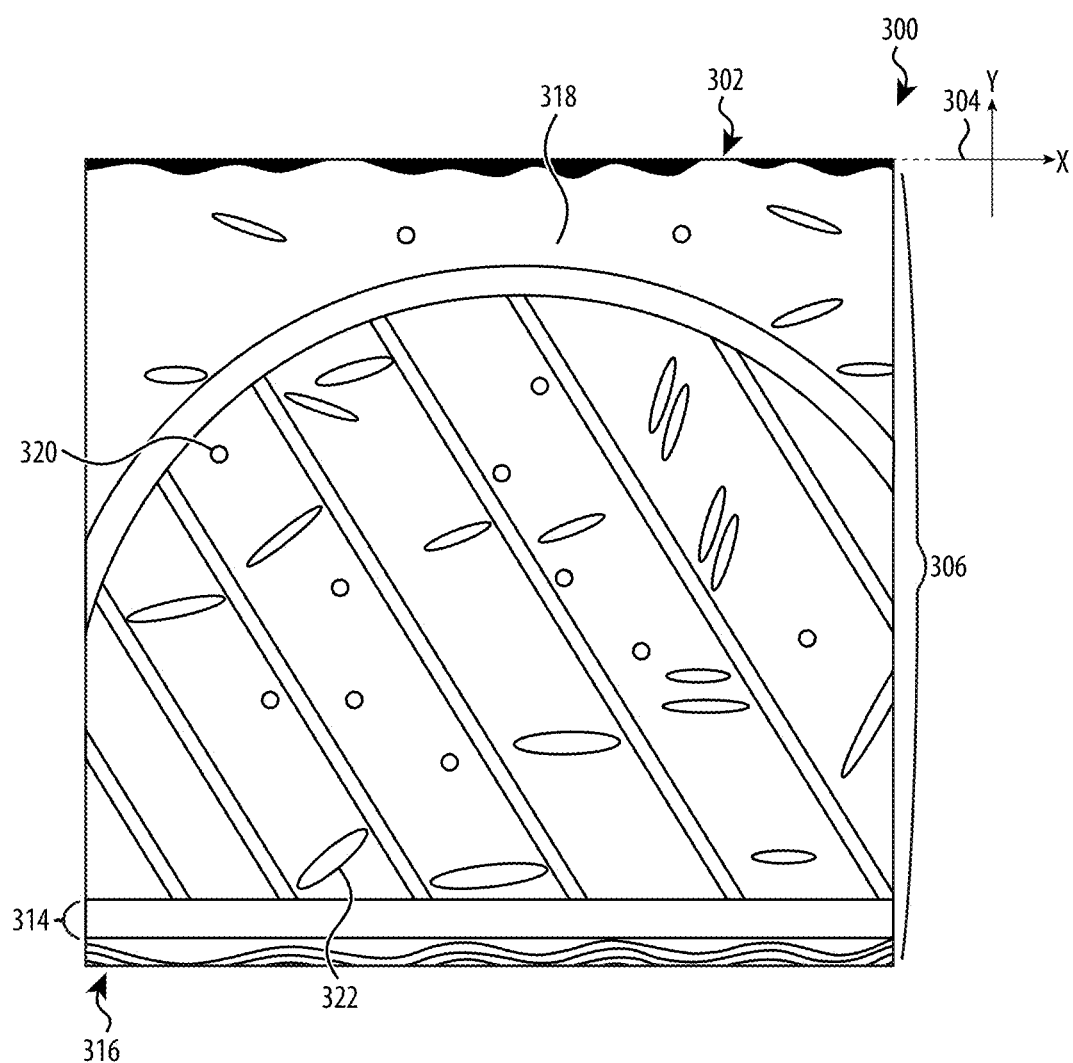
FIG. 3 depicts a conceptual illustration of an ultrasound scan of target tissues in accordance with at least one embodiment.
Figure 4:
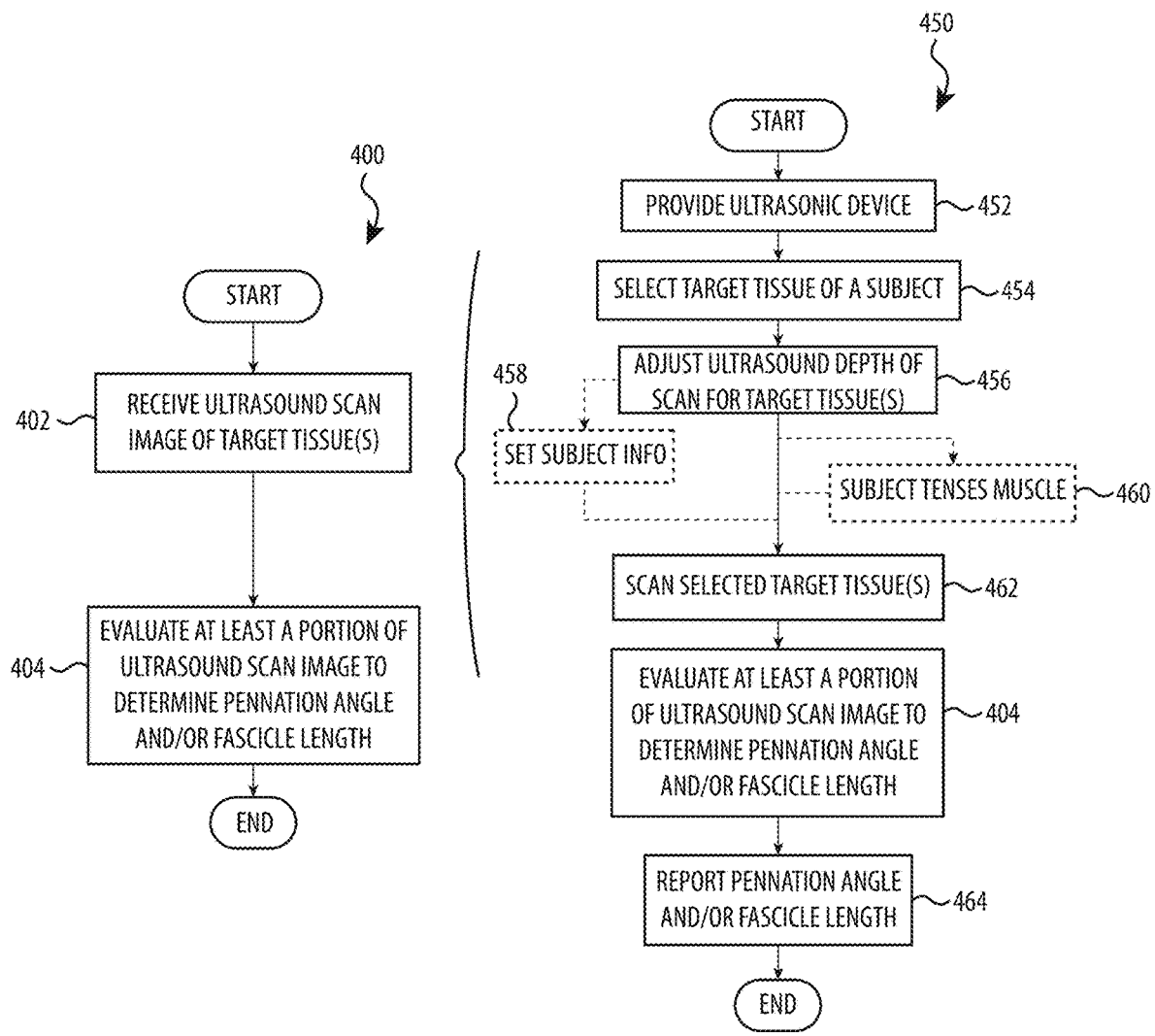
FIG. 4 depicts a high level flow diagram for a method of non-invasive determination of human pennation angle and/or fascicle length in accordance with at least one embodiment.
Figure 5:
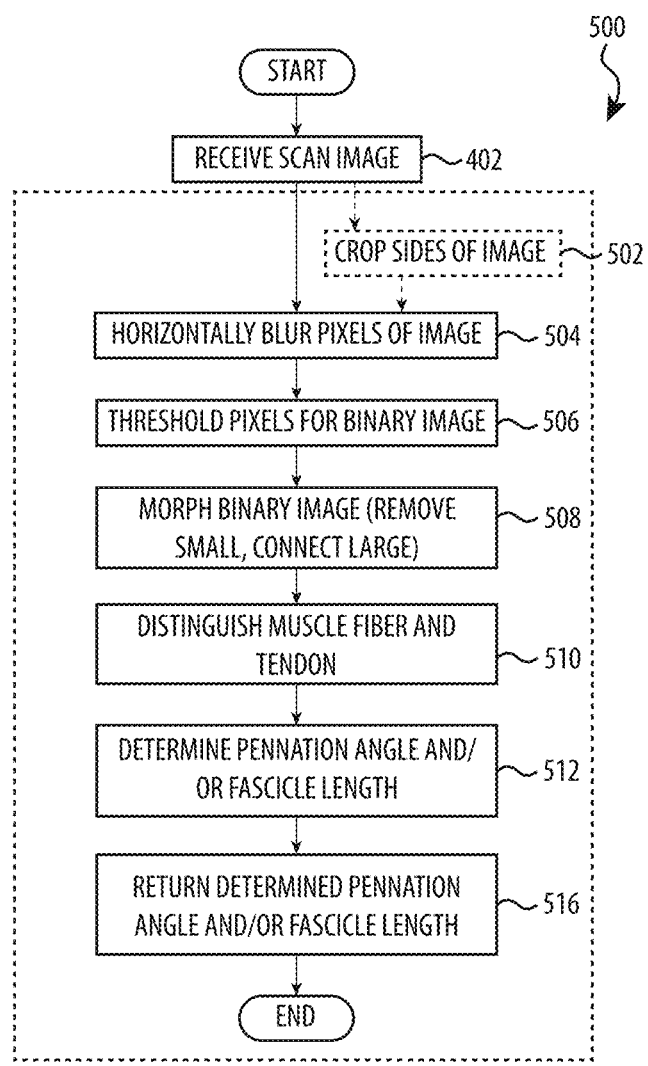
FIG. 5 depicts a refined flow diagram for the evaluating operation for non-invasive determination of human pennation angle and/or fascicle length in accordance with at least one embodiment.

FIGS. 4 and 5 in connection with FIGS. 2, 3 and 6-10 provide a high level flow diagram with conceptual illustrations depicting methods 400 and 500 for non-invasive determination of human pennation angle and/or fascicle length in accordance with at least one embodiment. It will be appreciated that the described method(s) need not be performed in the order in which it is herein described, but that this description is merely exemplary of one method of non-invasive determination of human pennation angle and/or fascicle length.

As is shown in FIG. 3, an enlarged conceptual ultrasound scan image 300 is shown. Typically ultrasound scan images are rendered in black and white in accordance with a grey scale, though color is certainly an option and within the scope of the present disclosure. Various structures within a subject's body reflect the ultrasound signal with varying intensity. In general there are two distinct patterns of reflection that give rise to the echoes that make up the ultrasound image—specular reflections and scattering reflections.

Specular reflections are responsible for the bright appearances of fibrous structures such as tendons, ligaments and the boundaries between different types of tissues. Scattering gives rise to the characteristic texture of an image seen within soft tissues. A scan image is composed of a plurality of pixels. Scan pixels may correlate directly with image pixels as used to render scan image 300. Of course, in some embodiments the resolution of the scan pixels may be greater than the resolution applied in the scan image, such that each pixel of the scan image may correlate to two or more pixels of the scan.

Those skilled in the art of ultrasound imaging can and often do perceive a great deal of information from images that are otherwise perhaps visually interesting but also perhaps largely unintelligible to the untrained eye.

Through image processing as performed by SNTA 200 and method 400, this training to perceive and differentiate structures within a typical ultrasound image is for all intents and purposes eliminated. For ease of discussion, conceptual rendering of ultrasound images has been provided to ease and facilitate this discussion.

Moreover, as shown in FIG. 3, the scan image 300 may capture a portion of the surface tissue 302, such as the skin at the top of the images, which defines a horizontal axis 304 for the scan image 300. The scan image 300 also shows at least a portion of subcutaneous tissues 306, which likely includes a body fat tissue, an as yet not clearly delineated area of muscle fibers, and other tissues such as fibrous tissues 314, 316 and so on, of which 318, 320 and 322 are exemplary.

Moreover, although scan image 300 provides enough information to discern the presence of body fat tissue, muscle fiber and other tissues, these tissues may not be sufficiently distinguished so as to permit accurate determination of muscle fiber pennation angle and/or fascicle length at this point. Indeed, embodiments of the present disclosure may apply image processing techniques so as to clearly distinguish muscle fiber and/or tendon to such a degree that highly accurate pennation angle and/or fascicle length measurements may be obtained.

As noted above and further described below, for at least one embodiment, between $\frac{1}{10}$th and $\frac{1}{5}$th of the image is vertically cropped from one or both sides so as to leave a more central portion of the scan image 300 for subsequent image processing. This cropping is more fully illustrated with respect to FIG. 6.

Further, although the illustrations and discussion provided herein for exemplary purposes generally appear to be 2D (two dimensional) images, the system and methods are equally applicable multi-axis ultrasound imaging techniques, such as for example 3D ultrasound.

FIG. 4 provides a high level flow diagram depicting a method 400 for non-invasive determination of pennation angle and/or fascicle length, which is more fully appreciated with respect to FIGS. 3 and 6-10 providing both real and conceptual illustrations of ultrasound scan images as processed in accordance with at least one embodiment. It will be appreciated that the described method, as well as all other subsequent methods and refinements to the disclosed methods need not be performed in the order in which they are herein described, but that the descriptions are merely exemplary of a method or methods that could be performed for non-invasive pennation angle and/or fascicle length determination.

As shown in FIG. 4, method 400 commences with receiving an ultrasound scan image of target tissue(s), block 402. An exemplary scan image such as scan image 300 is shown in FIG. 3. Moreover, even though muscle fiber and/or tendon may be the primary tissues of interest in one setting, for the pennation angle and/or fascicle length to be accurately determined under the present disclosure it may be desirable to distinguish the muscle fiber and/or tendon from other tissues. In addition, as the muscle fiber and/or tendon is captured in ultrasound scans that are often performed with an intent to image other tissues, such scan images may also be processed under the present disclosure for about real time or later analysis of pennation angle and/or fascicle length. Indeed, substantially real time analysis to determine a subject's pennation angle and/or fascicle length may be performed as a specific procedure, or as a beneficial ancillary procedure when a subject is undergoing an ultrasound imaging process for another purpose (such as determination of glycogen stores, determination of body fat, muscle tissue size, muscle quality, and so on).

Moreover, scan image 300 may be provided as described above through the use of SNTA 200 in an embodiment providing an ultrasound transducer 216, or through another ultrasound imaging system and/or process. For at least one embodiment the ultrasound scan image is provided by the system(s) and methods as set forth in U.S. Pat. No. 8,562, 529 entitled Method and System for Non-Invasive Determination of Glycogen Stores, U.S. Pat. No. 8,517,942 entitled Method for Non-Invasive Determination of Glycogen Stores, U.S. Pat. No. 8,512,247 entitled System for Non-Invasive Determination of Glycogen Stores, U.S. patent application Ser. No. 14/012,538 entitled System and Method for Target Muscle Glycogen Score Determination and Evaluation, and U.S. patent application Ser. No. 14/491,553 entitled System and Method for Non-Invasive Determination of Human Body Fat—each of which is incorporated herein by reference.

With the scan image 300 now received, method 400 continues with the evaluation of at least a portion of the scan image 300 to determine pennation angle and/or fascicle length, block 404. For application of method 400, an embodiment of SNTA 200 need not have, or otherwise be coupled to, an ultrasound transducer 216. Method 400 may also be performed by SNTA 200 when a user desires to review historical data of tissue scans, such as for example to revisit past histories of evaluation to perceive changes in development and potential adjustments to a subject's training methods, general activities, diet or other form of activity and/or medication.

Of course, for real time non-invasive determination of pennation angle and/or fascicle length, in varying embodiments SNTA 200 may indeed include an ultrasound transducer 216 as described above. As such, method 400 may be augmented as method 450, the augmentation as illustrated pertaining to at least one method of providing the received ultrasound scan image 300.

More specifically, for augmented method 450, an ultrasound transducer 216 is provided as part of SNTA 200, block 452. A target tissue, such as a muscle, e.g. target tissue(s) 208, is selected, block 454. As noted, the ultrasound transducer has an adjustable depth for scanning, such as a selection between about 0.5 and 10 centimeters. The ultrasound transducer 216 is adjusted to provide a depth of scan appropriate for the selected target tissue 208, block 456.

In at least one embodiment, the depth of scan is adjusted manually, such as to about 3.5 centimeters for the skin, body fat, and rectus femoris muscle. In an alternative embodiment, the depth of scan is automatically selected by an operator selecting a desired tissue, such as a muscle tissue, e.g., rectus femoris, vastus lateralis, or biceps. In addition, in varying embodiments, the auto-determined and set depth may also be adjustable by the operator so as to permit adjustment for various body types.

In at least one embodiment additional and optional information about the subject is recorded, as indicated by dotted block 458. This optional information may include, but is not limited to, details such as the subject's name, age, gender, time of day, status of subject—at rest/at VO2 Max, after eating, or other such information desired to be recorded and displayed in connection with the scanned image of the target muscle.

Moreover, to summarize for at least one embodiment, the augmented method 450 includes providing an ultrasound device having a movable transducer, the transducer operable in a high frequency range, selecting a target tissue 208 of a subject 212 and adjusting the ultrasound device for a depth of scan appropriate for the selected target tissue 208.

As the ultrasound transducer 216 operates by providing a high frequency signal that is directed into tissue and detecting reflections returned by encountered elements, it is understood and appreciated that the transducer should be aligned generally perpendicular to the selected target muscle. Of course, if a transducer having an alignment configuration that is other than perpendicular is employed, the specific alignment as intended for the transducer should be used.

It is understood and appreciated that an ultrasound transducer 216 may be positioned along the longitudinal or latitudinal axis of the tissue or somewhere in between. For general alignment purposes and ease of operation, in general the operator of the system will select ultrasound transducer 216 alignment matching to either the longitudinal or latitudinal axis of the target tissue 208.

Testing has determined that a key factor for deciding which alignment to use is perhaps the initial quality of the scan image. In other words, for at least one embodiment, at least a longitudinal and a latitudinal image of the target tissues is obtained so that the images can be compared by the operator and/or SNTA 200 to determine which image is best for analysis.

Application of the ultrasound transducer 216 against the subject's skin can be a practiced skill, for if too much pressure is applied the transducer may inadvertently compress the tissue and thereby hamper the quality of the scan and the resulting evaluation of pennation angle and/or fascicle length. However, an easy solution presents itself that substantially minimizes the risk of transducer related compression of the tissue.

As shown by optional dotted block 460, the subject can simply tense his or her muscle if it is the target tissue 208 or directly below the target tissue. More specifically, if the subject acts to tense his or her muscles adjacent to the desired target tissue, the natural action of the muscle contraction causes the muscle to swell and thereby resist compression. The contracted and thereby enlarged muscle may also be advantageous in providing an even clearer cross sectional scan than may be obtained with a relaxed muscle.

In short, while the quality of the scan for the tensed or un-tensed muscle adjacent to the target tissue 208 may be the same for an operator skilled in how much pressure to apply, for the novice, as well as the skilled operator, tensing an adjacent muscle does not appear to significantly hamper the determination of pennation angle and/or fascicle length and may help insure greater consistency of scans in a wide variety of locations and settings. Indeed, for at least one embodiment, when the method of scanning a target tissue(s) 208 is performed, the subject will tense his or her adjacent muscle as a normal and expected part of the scanning process.

Moreover, to achieve the scan of the target tissue 208, the ultrasound transducer 216 is disposed proximate to the target tissue 208 and as the ultrasound transducer 216 is activated the target tissue(s) 208 is scanned, block 462. In at least one embodiment the ultrasound transducer 216 is placed in direct contact with the subject's skin. In at least one alternative embodiment, a protective cover, shield or even the subject's clothing is disposed between the ultrasound transducer 216 and the subject's skin.

A scan image is then provided from the resulting scan, and evaluated as noted above, block 404. A report of the determined pennation angle and/or fascicle length may also be reported, block 464.

In other words, to summarize for at least one embodiment, the augmented method 450 continues with disposing the transducer proximate to the subject 212 and perpendicular to the selected target tissue 208, and then imaging the selected target tissue 208 by processing ultrasound reflection received by the transducer to provide at least a partial scan of the selected target tissue 208. Many ultrasound transducers provide images as cross sections of the tissues and structures whereas others may provide 3-D views. For consistency in analysis, in at least one embodiment the operator of SNTA 200 adopts a convention to scan a target tissue along its long axis or short axis.

For the majority of leg and arm tissues the long axis is generally parallel to bone structure and the short axis is generally perpendicular to bone structure. Indeed in some embodiments, scans with SNTA 200 may be performed substantially contemporaneously along both the long and short axes of a target tissue 208 for enhanced comparison and analysis.

Method 450 then continues with the evaluation of the scan as discussed above with respect to block 404. For at least one embodiment, it is understood and appreciated that the evaluation of the image 204 is performed about contemporaneously with the scanning of the target tissue 208.

The determined pennation angle and/or fascicle length is then reported to the operator, block 464. The determined pennation angle and/or fascicle length may also be recorded for use in plotting the changes in a subject's pennation angle and/or fascicle length over time, and/or in response to various different points of exercise, conditioning, diet, medication and other factors.

FIG. 5 in connection with FIGS. 6-10 provides a high level flow diagram with conceptual illustrations to further refine at least one embodiment of method 400 for evaluating at least a portion of the ultrasound scan image to determine pennation angle and/or fascicle length. Moreover in FIG. 5, method 500 corresponds in greater detail to block 404 of FIG. 4. Again, it is appreciated that the described method need not be performed in the order in which it is herein described, but that this description is merely exemplary of one method for non-invasive determination of human pennation angle and/or fascicle length.

More specifically, as FIG. 5 expands on FIG. 4, initially a scan image of the target tissues 208 is received, block 402. An exemplary image scan is conveniently provided as scan image 300 as shown and described above with respect to FIG. 3.

Figure 6:
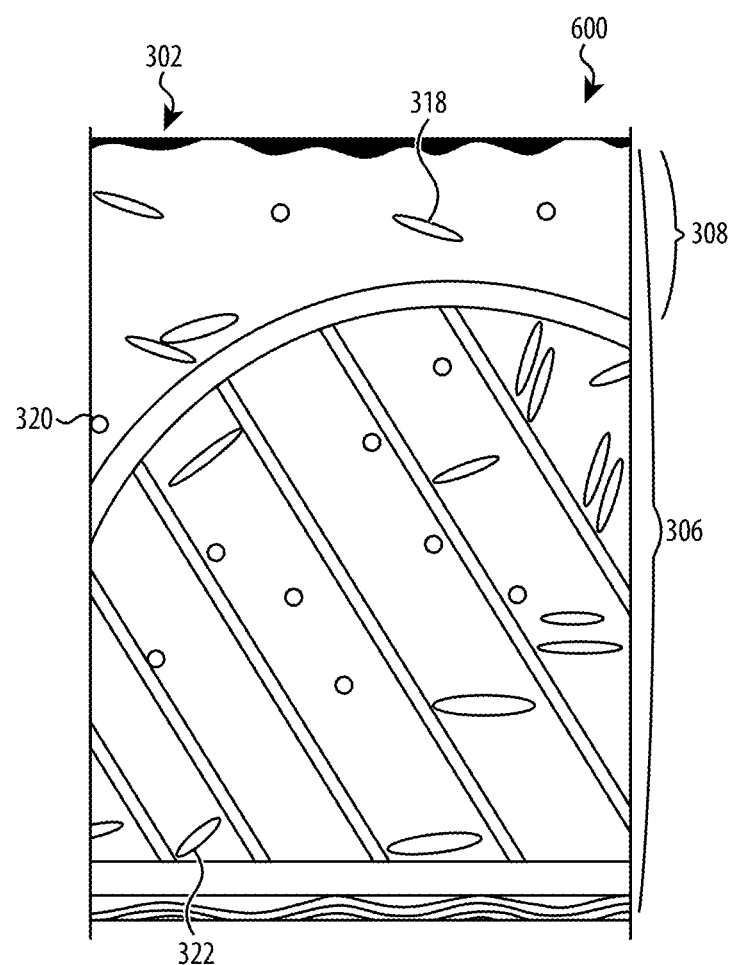
FIG. 6 depicts a conceptual illustration of a cropped ultrasound scan image in accordance with at least one embodiment.

Ultrasound scan images tend to image tissues directly below the transducer most clearly, with the side areas of the scan tending to be less clear. For purposes of subsequent image enhancement, for at least one embodiment one or both sides of the scan image 300 are cropped as is shown in FIG. 6 as cropped scan image 600. Moreover, cropped scan image 600 is the more central portion of scan image 300 shown in FIG. 3. Although embodiments of method 400 may be performed without side cropping, in general between ⅒ and ⅕ of the image is vertically cropped from each side as is suggested by dotted lines and optional block 502.

Figure 7:
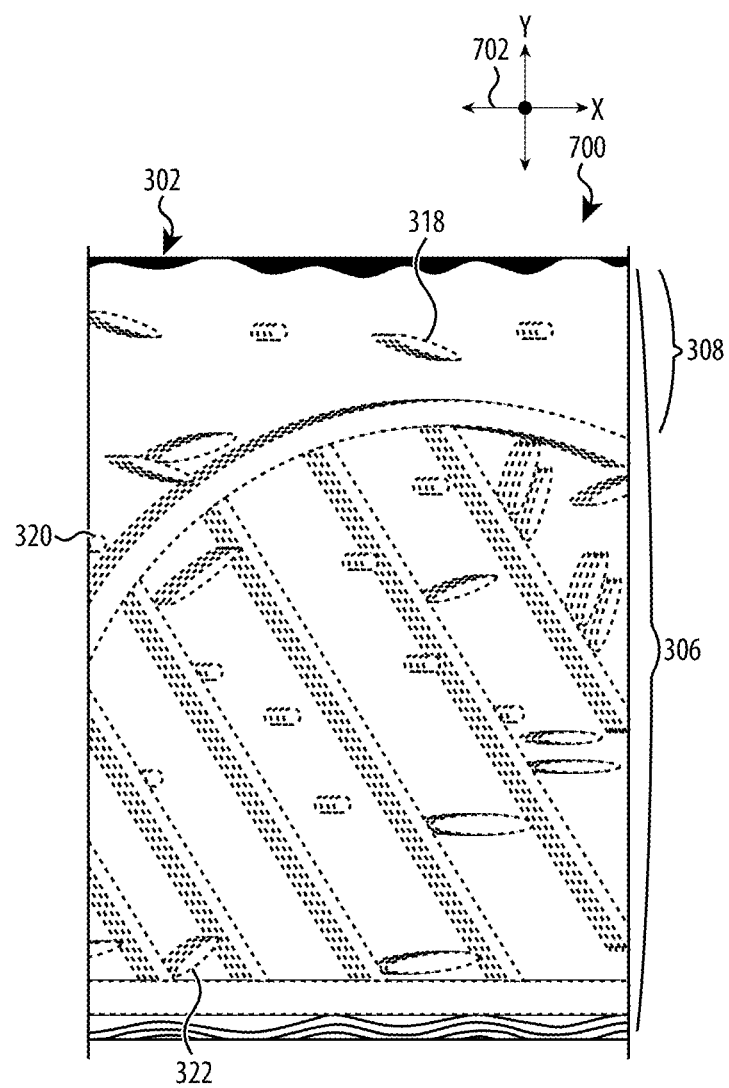
FIG. 7 depicts a conceptual illustration of a horizontally blurred ultrasound scan image in accordance with at least one embodiment.

Next, method 500 proceeds to horizontally blur and/or otherwise introduce noise into (such as vertical blur, speckling, and so on) the pixels as shown in the horizontally blurred scan image 700 shown in FIG. 7, block 504 (see FIG. 5).

Traditionally the clarity of an ultrasound image and indeed the sharpness of the elements within the ultrasound image are very important. This is quite understandable as oftentimes an ultrasound image is used to guide a doctor in surgery, so clear imaging is important for both the doctor and the patient.

For the present disclosure, sharpness of detail within the image may not be important. In fact, the present disclosure teaches how image processing techniques may be applied so as to remove elements of small detail and enhance the ultimate distinguishing of muscle fiber and/or tendon. In image processing, a kernel such as a convolution matrix, mask or filter is a small matrix that can be applied to propagate a change in a source image for a desired effect. Moreover the change imparted is a result of convolution between an applied kernel and an image.

Blurring is an image processing technique commonly applied so as to reduce noise and reduce detail. Blurring functions are well understood and known to those skilled in the art and need not be discussed in detail here.

A high level discussion of blurring is provided so as to facilitate general understanding of the process so as to further appreciate the advantageous achievement of SNTA 200 and method 400. In simple terms blurring an object means that each of the pixels in the source image gets spread over and mixed with surrounding pixels. With respect to the present disclosure, blurring may be achieved by application of a Mean Filter, Weighted Average Filter, Gaussian Filter or other appropriate filter. A Mean Filter is also known as a Box Filter or Average Filter, and is understood to have the following properties—it is odd ordered, the sum of all elements should be 1 and the elements of the filter are the same. A Weighted Average Filter acts as the name implies—giving more weight to the center value. Here again it is odd ordered, the sum of all elements should be 1, but the weight of the center element should be more than all of the other elements. A Gaussian Filter is one that uses a Gaussian function, which also expresses the normal distribution in statistics, for calculating the transformation to apply to each pixel in the image.

For purposes of the present disclosure, blurring is only to be applied along the horizontal axis. As such a 1×3 Mean Filter or a one dimension Gaussian Function is typically appropriate. For at least one embodiment, the blurring filter is a 1 dimensional Gaussian function:

$$G(x) = \frac{1}{\sqrt{2\pi\sigma^2}} e^{-\frac{x^2}{2\sigma^2}}$$

For at least one alternative embodiment, a 1×3 Mean Filter such as [⅓, ⅓, ⅓] is applied.

As is shown in FIG. 7, in conceptually blurred image 700, the tissue elements such as 322 have been blurred along the horizontal X axis as indicated by coordinate axis 702. No blurring has occurred along the vertical Y axis. As such the edge distinctions along the horizontal axis are less sharp as blurring makes the collections of similar pixels either bigger or smaller.

Figure 8:
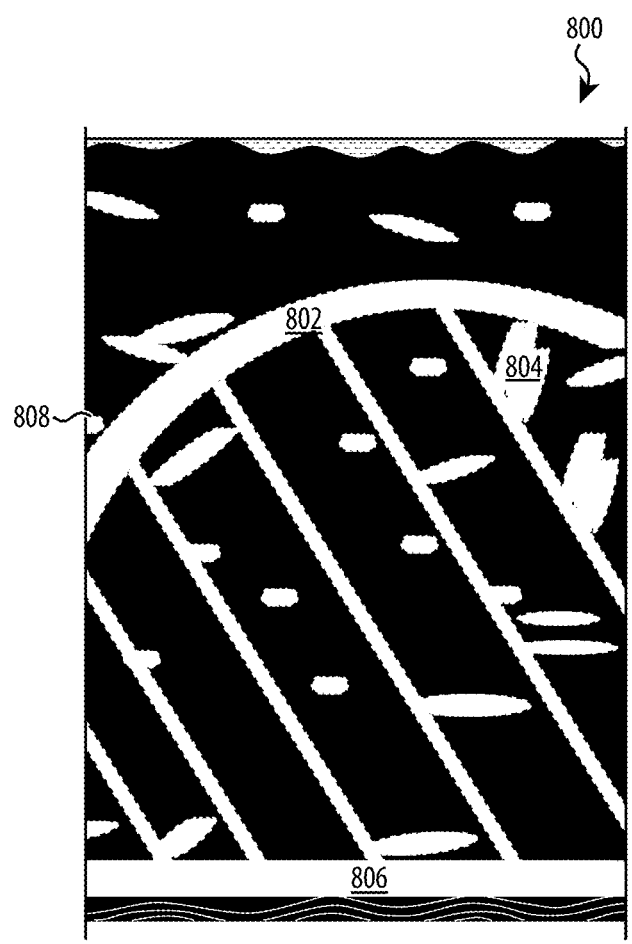
FIG. 8 depicts a conceptual illustration of a thresholded horizontally blurred image to provide a binary image in accordance with at least one embodiment.

Next, method 500 proceeds to threshold the pixels of the blurred image 700 to either black or white to provide a binary image 800, block 506, as shown in FIG. 8.

Thresholding is a method of image segmentation and is well known to those skilled in the art and need not be discussed in detail herein. A high level discussion of thresholding is provided so as to facilitate general understanding of the process so as to further appreciate the advantageous achievement of SNTA 200 and method 400. From a gray scale image, thresholding may be used to create a binary image, such as binary image 800 from blurred scan image 700.

More specifically, each pixel of the blurred scan image 700 has a value equal to or ranging from black (i.e., 0) to white (i.e., 255). To threshold the pixels, those above a midpoint (i.e., 127) are reset to white (i.e., 255) while those pixels at or below the midpoint (i.e., 127) are reset to black (i.e., 0). Of course this scale is merely exemplary and an alternative scale may be used. In addition, although color is the attribute for thresholding as described herein, in alternative embodiments thresholding may be applied to another color, luminance, darkness, contrast or other identifiable attribute of each pixel. Further, although thresholding is discussed using the midpoint, use of other threshold values is possible and contemplated. In various implementations, the threshold value may be set according to the particular apparatus used to obtain the image.

Moreover the present disclosure is further processing the scan image so as to provide a binary image that has only two possible values for each pixel. The remaining elements, of which elements 802, 804, 806 and 808 are exemplary, are crisp white elements with very discernable edges.

Next, method 500 proceeds to morph the remaining elements of the binary image 800 to remove small elements and connect large elements. To "morph" or "morphing" refers to mathematical morphology—a technique for the analysis and processing of geometric structures based on set theory, lattice theory, topology and or random functions and is a known technique applied to digital images. The basic morphological operators or morphological functions as they are also known are erosion, dilation, opening and closing. These morphological functions are well known to those skilled in the art and need not be discussed in detail herein.

A high level discussion of morphing, a.k.a. mathematical morphology, is provided so as to facilitate general understanding of the process so as to further appreciate the advantageous achievement of SNTA 200 and method 400.

The basic idea in binary morphology of a binary image is to probe an image with a simple, predefined shape such as a disc, square, cross or other simple geometric shape which is referred to as a structuring element and is itself a binary image. Opening removes white "holes" while closing removes black "holes." In accordance with at least one embodiment, the morphological function applied to further process the scan image so as to distinguish the muscle fiber and/or tendon is the morphological function of opening.

Opening is obtained by eroding an image followed by then dilating the image. The erosion of a binary image A (the binary image 800) by the structuring element B (a disc of radius r) in Euclidean space E=Rd is generally understood by the equation:

$$A \ominus B = \{z \varepsilon E | B z \subset A\}$$

where Bz is the translation of B by the vector Z, i.e.:

$$Bz = \{b + z | b \varepsilon B\}, \forall z \varepsilon E.$$

When the structuring element B such as a square or disc has a center located on the origin E, the erosion of A by B can be understood as the locus of points reached by the center of B when B moves inside A.

The erosion of A by B is also given by the expression:

$$A \ominus B = \cap_{b \varepsilon B} A_{-b}$$

The dilation of A by the structuring element B is defined by:

$$A \oplus B = \cup_{b \varepsilon B} A_b$$

The dilation is commutative, also given by:

$$A \oplus B = B \oplus A = \cup_{a \varepsilon A} B_a$$

As before, when the structuring element B such as a square or disc has a center located on the origin E, the dilation of A by B can be understood as the locus of the points covered when the center of B moves inside A.

Figure 9:
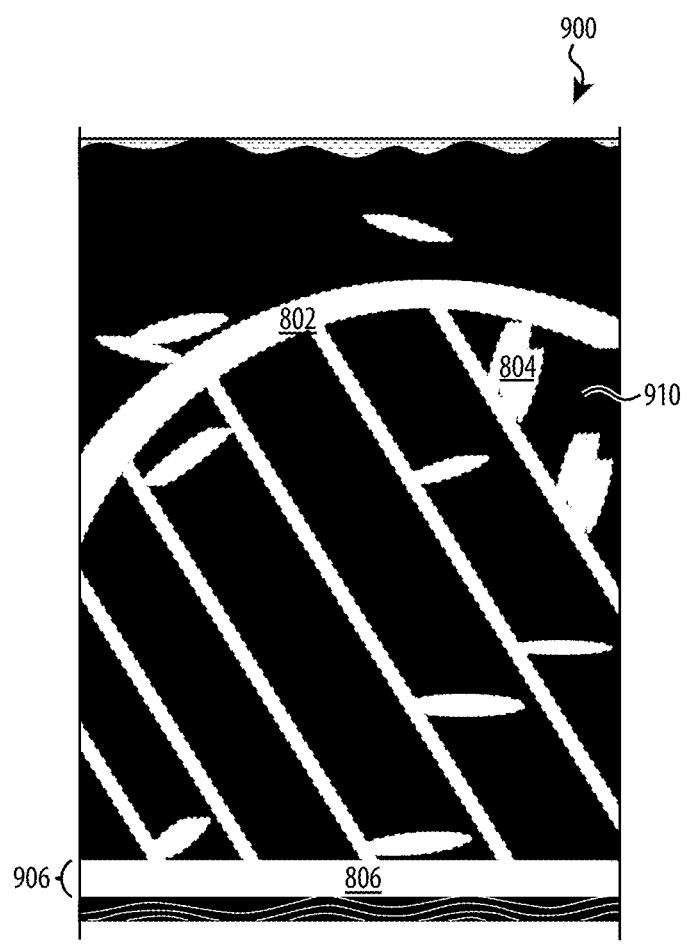
FIG. 9 depicts a conceptual illustration of a morphed image provided from the binary image in accordance with at least one embodiment.

More simply stated, for at least one embodiment the morphological function of opening is applied so as to further reduce the number of "white" elements within the binary image 800 so as to result in a reduced element image shown as morphed image 900, shown in FIG. 9.

Comparing morphed image 900 to binary image 800 it can and will be seen that the majority of smaller white elements, such as element 808 shown in FIG. 7, have been removed by the morphing process in providing morphed image 900.

With the elements of the processed binary image now further reduced it is quite clear that this morphed image 900 is distantly related to original scan image 204. However, because of the binary nature of morphed image 900 and the reduced number of elements, morphed image 900 is advantageously poised to permit the identification and distinguishing muscle fiber 910 and tendon 906 within the morphed image 900, block 510. Various techniques may be used to distinguish the muscle fiber 910 and the tendon 906 from other remaining elements in the morphed image 1000.

Figure 10:
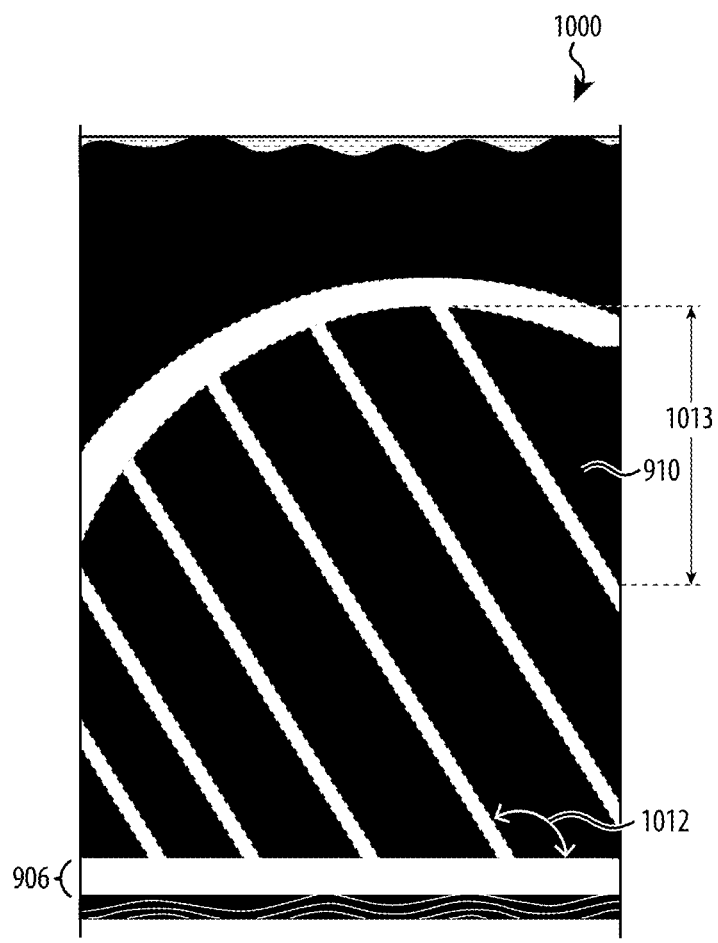
FIG. 10 depicts a conceptual illustration of the resulting processed image for non-invasive determination of human pennation angle and/or fascicle length in accordance with at least one embodiment.

With the muscle fiber 910 and tendon 906 now distinguished, the non-relevant layers may be further removed, for the resulting highly processed image 1000 shown in FIG. 10. A determination of pennation angle 1012 between the muscle fiber 910 and the tendon 906 is now permitted with a high degree of precision. Additionally or alternatively, a determination of the fascicle length 1013 of the muscle fiber 910 is also now permitted with a high degree of precision.

For example, once the tendon 906 and the muscle fiber 910 are distinguished, the major axis of each structure may be identified. In some implementations, axes of multiple muscle fibers 910 may be identified and combined (such as average, mean, and so on) to obtain a more accurate major axis for the muscle fiber 910. The major axes of the muscle fiber 910 and the tendon 906 may then be compared to determine the pennation angle. In some implementations, a reference angle may be established against which the axes are compared to determine the pennation angle.

Similarly, the fascicle length may be determined based on the major axis of the muscle fiber 910, the position of the ends of the muscle fiber 910 with respect to the tendon 906, and so on. Various methodologies may be used in determining pennation angle and/or fascicle length based on the distinguished muscle fiber 910 and tendon 906.

To briefly summarize, for at least one embodiment the method of non-invasive determination of human pennation angle and/or fascicle length includes receiving at least one ultrasound scan image (block 402) of at least a portion of a skin layer as disposed above one or more additional tissue layers, the image provided by a plurality of pixels; blurring (and/or otherwise introducing noise into) the pixels of the image (block 504); thresholding the pixels of the image to provide a binary image having a plurality of structural elements of different sizes (block 506); morphing the structural elements of the binary image to remove small structural elements and connect large structural elements (block 508); distinguishing muscle fiber and/or tendon from remaining structural elements (block 510); and determining the pennation angle and fascicle length based on the muscle fiber and tendon (block 512).

With the pennation angle and/or fascicle length now determined, method 500 may return the determined pennation angle and/or fascicle length to the operator, block 516. Various information based upon the determined pennation angle and/or fascicle length may also be returned to the operator.

For example, a pennation angle and/or fascicle length rating may be returned to the operator. In some implementations, the pennation angle and/or fascicle length rating may involve a scale, such as a rating between "small" and "large," a rating between "good" and "poor," a value between 1 and 100, and so on. The pennation angle and/or fascicle length rating may be based on comparison of pennation angle and/or fascicle length to previously measured or a historical pennation angle and/or fascicle length (such as where analysis is repeated over time upon additional scan images to evaluate the pennation angle and/or fascicle length over time), comparison to other subjects (such as subjects with similar characteristics like age, gender, occupation, sport, and so on), comparison to one or more pennation angle and/or fascicle length goals (such as a performance objective to increase pennation angle and/or fascicle length, balance pennation angle and/or fascicle length in similar muscles, and so on), comparison of pennation angle and/or fascicle length to that of a similar muscle (such as the left bicep to the right bicep), and so on. Any of this data to which the pennation angle and/or fascicle length may be compared may be retrieved from one or more storage medium in order for the comparison to be performed.

By way of another example, advice based on the pennation angle and/or fascicle length may also be returned to the operator. In some implementations, advice regarding training, food, and/or other parameters may be based on comparison of the pennation angle and/or fascicle length to a desired pennation angle and/or fascicle length or pennation angle and/or fascicle length goal. For example, advice regarding performance of specific exercises, additional weight or repetitions, increased or decreased protein, increased or decreased carbohydrates, and so on may be returned when the pennation angle and/or fascicle length is below the desired pennation angle and/or fascicle length or pennation angle and/or fascicle length goal, above the desired pennation angle and/or fascicle length or pennation angle and/or fascicle length goal, and so on. Specific advice to return based on the results of a comparison, as well as the comparison results under which to return such advice, may be retrieved from one or more storage medium.

The determination of pennation angle and/or fascicle length as provided by SNTA 200 and/or methods 400 and 500 is applicable in a wide variety of qualified formulas for the determination of a number of different values which may be used by the subject or subject's doctor, trainer, caretaker, or other in a variety of different ways.

FIGS. 11, 12, and 13A-13C in connection with FIGS. 14A-14K provide a high level flow diagram with conceptual illustrations depicting methods 1100, 1200, 1300A, 1300B, and 1300C for determining pennation angle. It will be appreciated that the described method(s) need not be performed in the order in which it is herein described, but that this description is merely exemplary of one method of non-invasive determination of human pennation angle and/or fascicle length. One or more of the methods 1100, 1200, 1300A, 1300B, and 1300C may be performed by the SNTA 200 of FIG. 2.

Figure 11:
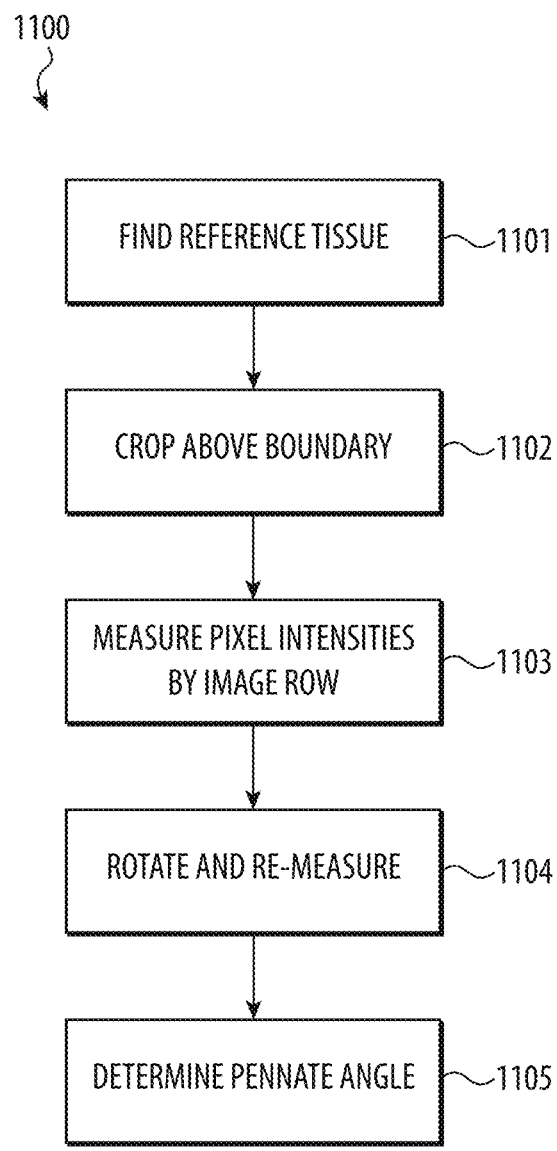
FIG. 11 depicts a first example method of determining pennation angle.

FIG. 11 depicts a first example method 1100 of determining pennation angle. At 1101, a reference tissue is found in an ultrasound scan image of target tissue(s). For example, the reference tissue may be the fascial boundary between a rectus femoris muscle and vastus intermedius muscle, between a vastus lateralis muscle and vastus intermedius muscle, and so on. In some examples, it may be ensured that the reference tissue is horizontal in the scan image (such as with respect to a skin layer that defines a horizontal axis for the ultrasound scan image). In other examples, an angle for the reference tissue may be determined and then used as an offset from horizontal to correct a determined pennate angle.

At 1102, the ultrasound scan image may be cropped above a boundary. For example, if the reference tissue is the fascial boundary between a rectus femoris muscle and vastus intermedius muscle, the ultrasound scan image may be cropped above the rectus femoris muscle. By way of another example, if the reference tissue is the facial boundary between vastus lateralis muscle and vastus intermedius muscle, the ultrasound scan image may be cropped above the vastus lateralis muscle.

At 1103, pixel intensities in pixels of the cropped ultrasound scan image may be measured by row in the cropped ultrasound scan image. At 1104, the cropped ultrasound scan image may be rotated and pixel intensities in pixels of the cropped ultrasound scan image may be re-measured.

At 1105, the pennate angle may be determined for the target tissue. The pennate angle may be the row of the cropped ultrasound scan image with the brightest pixel intensity.

In various examples, the pennate measurements may be tracked and monitored for a subject. The pennate measurements may be tracked and monitored over time to compare changes over time, differences to pennate measurements of other muscles, and so on. The pennate measurements may be compared to pennate measurements of other subjects or other data to relate the subject to various healthy/at risk categories, as a component of determining overall muscle health for the subject including various other information (such as glycogen scores, body fat amounts, muscle tissue size, hydration, and so on), and so on. Such information may be presented and/or used to advise the subject regarding health, changes to exercise, training, diet, or other regimen in view of a goal, and so on.

Although the example method 1100 is illustrated and described as including particular operations performed in a particular order, it is understood that this is an example. In various implementations, various orders of the same, similar, and/or different operations may be performed without departing from the scope of the present disclosure.

For example, the example method 1100 is illustrated and described as measuring pixel intensities. However, other pixel attributes may be evaluated rather than pixel intensity to determine pennate angle. Various configurations are possible and contemplated without departing from the scope of the present disclosure.

By way of another example, the example method 1100 is illustrated and described as cropping the ultrasound scan image and determining the pennate angle by analyzing the cropped ultrasound scan image. However, in various examples, pennate angle may be determined by analyzing an uncropped ultrasound scan image.

Figure 12:
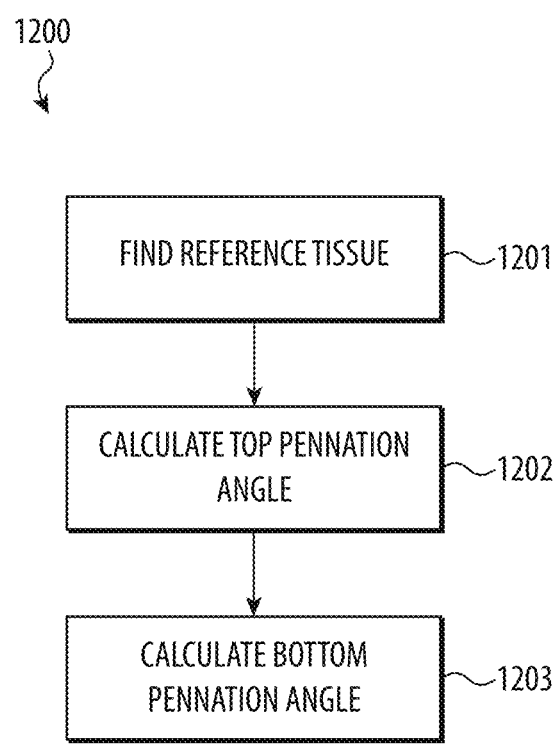
FIG. 12 depicts a second example method of determining pennation angle.

FIG. 12 depicts a second example method 1200 of determining pennation angle. At 1201, a reference tissue is found in an ultrasound scan image of target tissue(s). For example, the reference tissue may be the fascial boundary between a rectus femoris muscle and vastus intermedius muscle, between a vastus lateralis muscle and vastus intermedius muscle, and so on. In various implementations, finding the reference tissue may include cropping sides of the ultrasound scan image (such as sides with respect to a horizontal axis defined by a skin layer), horizontally blurring and/or otherwise introducing noise into the cropped ultrasound scan image, thresholding the blurred ultrasound scan image to black and white, morphologically opening the thresholded ultrasound scan image to remove small objects, computing features of the thresholded ultrasound scan image, finding a reference fascia feature using the computed features, and measuring the angle of the reference fascia feature. Such cropping, blurring, thresholding, feature computation, and so on may be performed using similar techniques to those discussed above with respect to FIGS. 3-10.

At 1202, a top pennation angle may be calculated for the reference tissue. "Top" may be with respect to a horizontal axis defined by a skin layer. In various implementations, calculating the top pennation angle may include cropping the ultrasound scan image above a fascia boundary (such as above the rectus femoris muscle, the vastus lateralis muscle, and so on), blurring and/or otherwise introducing noise into the cropped ultrasound scan image, thresholding the blurred ultrasound scan image, computing features of the thresholded ultrasound scan image, finding features using the computations, measuring angles of the found features, and determining the top pennation angle by subtracting the angle of the reference fascia feature from the highest 75% of the measured angles of the found features. Such cropping, blurring, thresholding, feature computation, and so on may be performed using similar techniques to those discussed above with respect to FIGS. 3-10.

At 1203, a bottom pennation angle may be calculated for the reference tissue. "Bottom" may be with respect to a horizontal axis defined by a skin layer. In various implementations, calculating the bottom pennation angle may include cropping the ultrasound scan image below a fascia boundary (such as above the rectus femoris muscle, the vastus lateralis muscle, and so on), blurring and/or otherwise introducing noise into the cropped ultrasound scan image, thresholding the blurred ultrasound scan image, computing features of the thresholded ultrasound scan image, finding features using the computations, measuring angles of the found features, and determining the bottom pennation angle by subtracting the angle of the reference fascia feature from the highest 25% of the measured angles of the found features. Such cropping, blurring, thresholding, feature computation, and so on may be performed using similar techniques to those discussed above with respect to FIGS. 3-10.

In various examples, the pennate measurements may be tracked and monitored for a subject. The pennate measurements may be tracked and monitored over time to compare changes over time, differences to pennate measurements of other muscles, and so on. The pennate measurements may be compared to pennate measurements of other subjects or other data to relate the subject to various healthy/at risk categories, as a component of determining overall muscle health for the subject including various other information (such as glycogen scores, body fat amounts, muscle tissue size, hydration, and so on), and so on. Such information may be presented and/or used to advise the subject regarding health, changes to exercise, training, diet, or other regimen in view of a goal, and so on.

Although the example method 1200 is illustrated and described as including particular operations performed in a particular order, it is understood that this is an example. In various implementations, various orders of the same, similar, and/or different operations may be performed without departing from the scope of the present disclosure.

For example, the example method 1200 is illustrated and described as calculating both the top and the bottom pennation angles, it is understood that this is an example. In some implementations, either the top or the bottom pennation angle may be calculated instead of both without departing from the scope of the present disclosure.

Figure 13A:
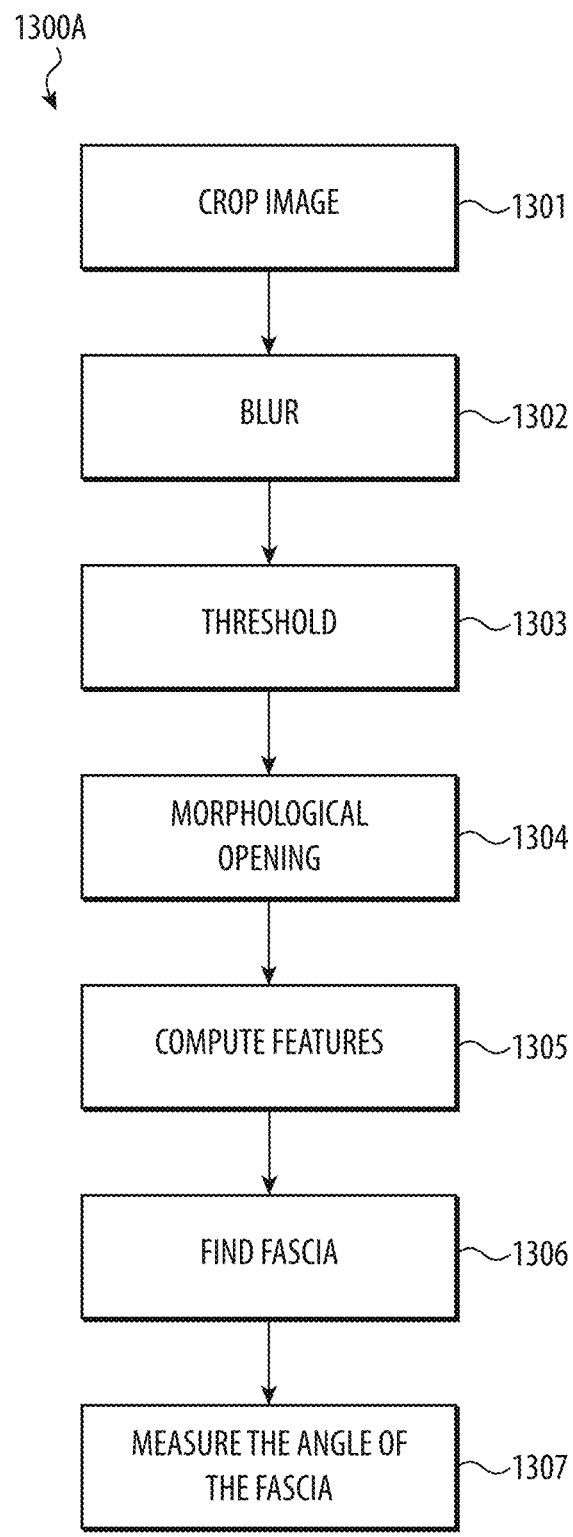
FIG. 13A depicts an example expansion of the operation of finding reference tissue in the second example method illustrated in FIG. 12.

FIG. 13A depicts an example expansion 1300A of the operation of finding reference tissue at 1201 in the second example method illustrated in FIG. 12.

At 1301, sides of an ultrasound scan image of target tissue(s) (such as sides with respect to a horizontal axis defined by a skin layer) may be cropped. At 1302, the cropped ultrasound scan image may be horizontally blurred and/or noise may be otherwise introduced into the cropped ultrasound scan image. At 1303, the blurred ultrasound scan image may be thresholded to black and white. At 1304, the thresholded ultrasound scan image may be morphologically opened to remove small objects.

At 1305, features of the thresholded ultrasound scan image may be computed. Computing the features may include evaluating the area of features, the major axis length of features, the mean pixel intensity of the features, the center of mass of features, and so on. At 1306, a reference fascia feature may be found using the computed features. At 1307, the angle of the reference fascia feature may be measured. The measured angle of the reference fascia feature may be used further with respect to 1300B and/or 1300C discussed below.

1301-1307 discuss cropping, blurring, thresholding, feature computation, and so on. Such cropping, blurring, thresholding, feature computation, and so on may be performed using similar techniques to those discussed above with respect to FIGS. 3-10.

Although the example expansion 1300A is illustrated and described as including particular operations performed in a particular order, it is understood that this is an example. In various implementations, various orders of the same, similar, and/or different operations may be performed without departing from the scope of the present disclosure.

For example, the example expansion 1300A is illustrated and described as cropping the ultrasound scan image, it is understood that this is an example. In various implementations, the ultrasound scan image may be analyzed to determine the angle of a reference fascia feature without cropping.

Figure 13B:
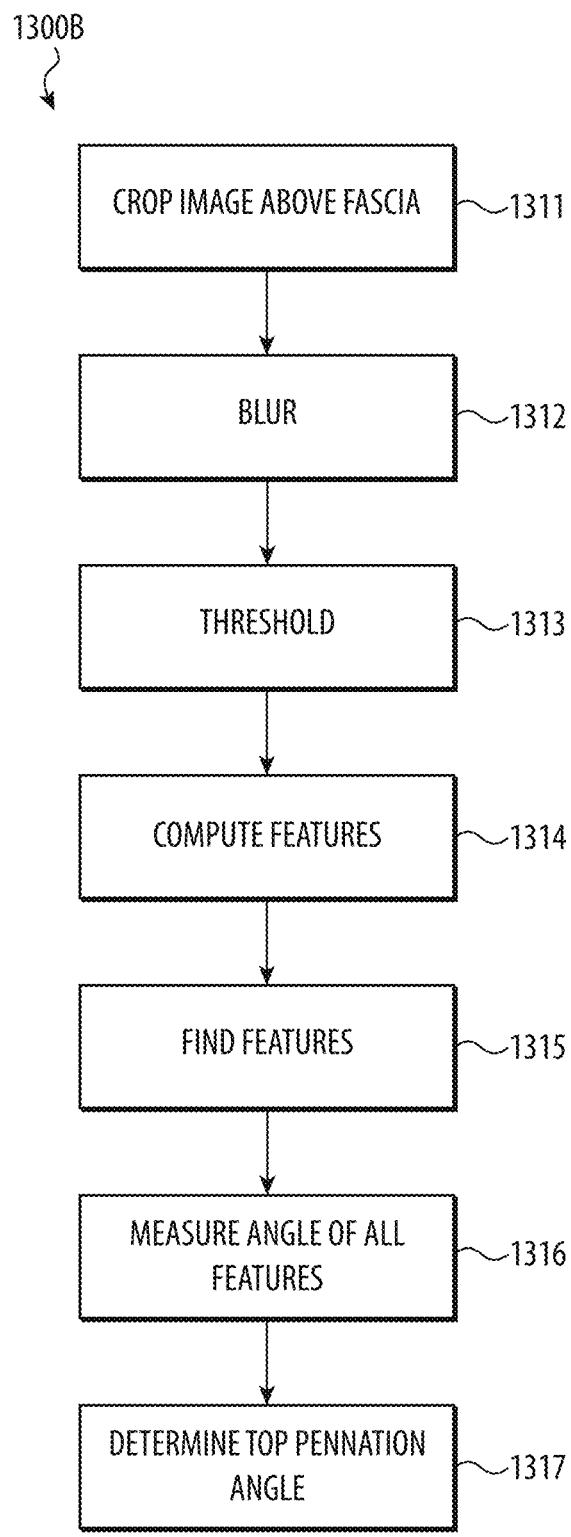
FIG. 13B depicts an example expansion of the operation of calculating the top pennation angle in the second example method illustrated in FIG. 12.

FIG. 13B depicts an example expansion 1300B of the operation of calculating the top pennation angle at 1202 in the second example method illustrated in FIG. 12.

At 1311 the ultrasound scan image may be cropped above a fascia boundary (such as above the rectus femoris muscle, the vastus lateralis muscle, and so on). At 1312, the cropped ultrasound scan image may be blurred and/or noise may be otherwise introduced into the cropped ultrasound scan image. At 1313, the blurred ultrasound scan image may be thresholded.

At 1314, features of the thresholded ultrasound scan image may be computed. Computing the features may include evaluating the eccentricity of features, the area of features, and so on. At 1315, features may be found using the computations. At 1316, angles of the found features may be measured. At 1317, the top pennation angle may be determined by subtracting the angle of the reference fascia feature from the highest 75% of the measured angles of the found features.

1311-1317 discuss cropping, blurring, thresholding, feature computation, and so on. Such cropping, blurring, thresholding, feature computation, and so on may be performed using similar techniques to those discussed above with respect to FIGS. 3-10.

Although the example expansion 1300B is illustrated and described as including particular operations performed in a particular order, it is understood that this is an example. In various implementations, various orders of the same, similar, and/or different operations may be performed without departing from the scope of the present disclosure.

For example, the example expansion 1300B is illustrated and described as analyzing the original ultrasound scan image used in the example expansion 1300A previous to any of the processing discussed in the example expansion 1300A, it is understood that this is an example. In various implementations, various versions of the ultrasound scan image may be analyzed to determine the top pennation angle without departing from the scope of the present disclosure.

By way of another example, 1317 is described as determining the top pennation angle by subtracting the angle of the reference fascia feature from the highest 75% of the measured angles of the found features. However, it is understood that this is an example. In various implementations, the angle of the reference fascia feature may be subtracted from the measured angles of all of the found features or any subset thereof and/or the measured angles of all of the found features or any subset thereof may be otherwise used to determine the top pennation angle without departing from the scope of the present disclosure.

Figure 13C:
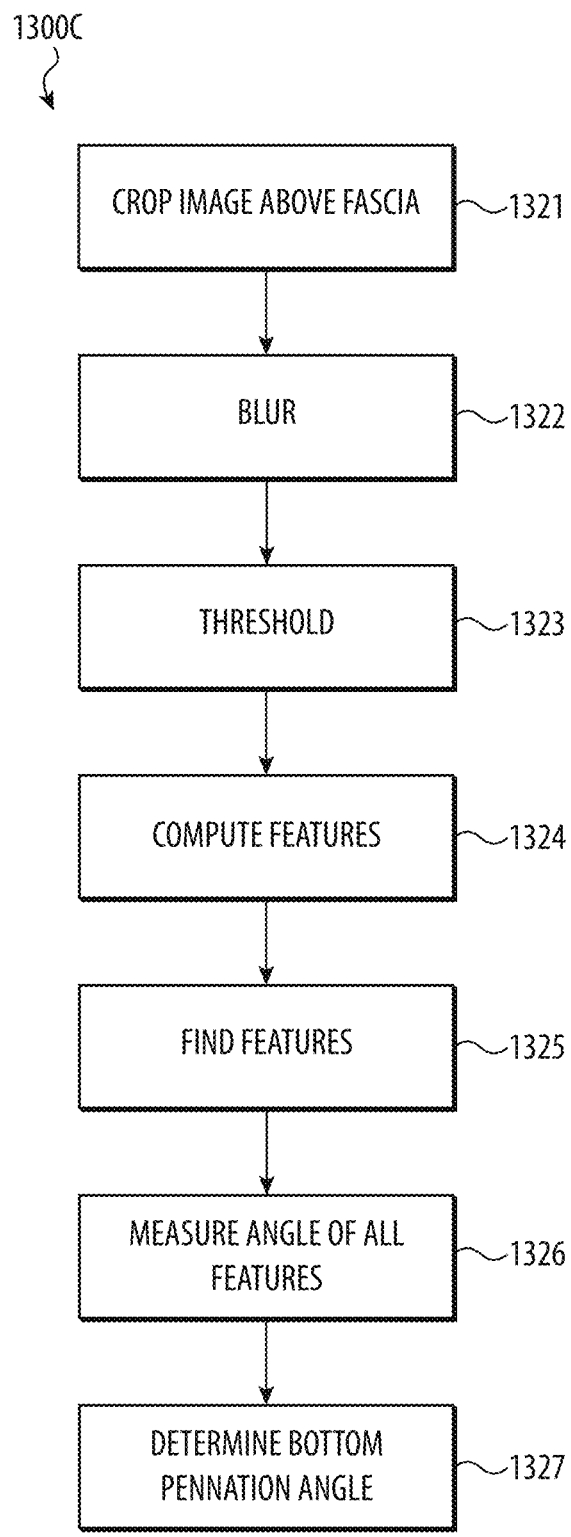
FIG. 13C depicts an example expansion of the operation of calculating the bottom pennation angle in the second example method illustrated in FIG. 12.

FIG. 13C depicts an example expansion 1300C of the operation of calculating the bottom pennation angle at 1203 in the second example method illustrated in FIG. 12.

At 1321 the ultrasound scan image may be cropped below a fascia boundary (such as above the rectus femoris muscle, the vastus lateralis muscle, and so on). At 1322, the cropped ultrasound scan image may be blurred and/or noise may be otherwise introduced into the cropped ultrasound scan image. At 1323, the blurred ultrasound scan image may be thresholded.

At 1324, features of the thresholded ultrasound scan image may be computed. Computing the features may include evaluating the eccentricity of features, the area of features, and so on. At 1325, features may be found using the computations. At 1326, angles of the found features may be measured. At 1327, the top pennation angle may be determined by subtracting the angle of the reference fascia feature from the highest 25% of the measured angles of the found features.

1321-1327 discuss cropping, blurring, thresholding, feature computation, and so on. Such cropping, blurring, thresholding, feature computation, and so on may be performed using similar techniques to those discussed above with respect to FIGS. 3-10.

Although the example expansion 1300C is illustrated and described as including particular operations performed in a particular order, it is understood that this is an example. In various implementations, various orders of the same, similar, and/or different operations may be performed without departing from the scope of the present disclosure.

For example, the example expansion 1300C is illustrated and described as analyzing the original ultrasound scan image used in the example expansions 1300A, 1300B previous to any of the processing discussed in the example expansion 1300A of the example expansion 1300B, it is understood that this is an example. In various implementations, various versions of the ultrasound scan image may be analyzed to determine the bottom pennation angle without departing from the scope of the present disclosure.

By way of another example, 1327 is described as determining the top pennation angle by subtracting the angle of the reference fascia feature from the highest 25% of the measured angles of the found features. However, it is understood that this is an example. In various implementations, the angle of the reference fascia feature may be subtracted from the measured angles of all of the found features or any subset thereof and/or the measured angles of all of the found features or any subset thereof may be otherwise used to determine the top pennation angle without departing from the scope of the present disclosure.

Figure 14A:
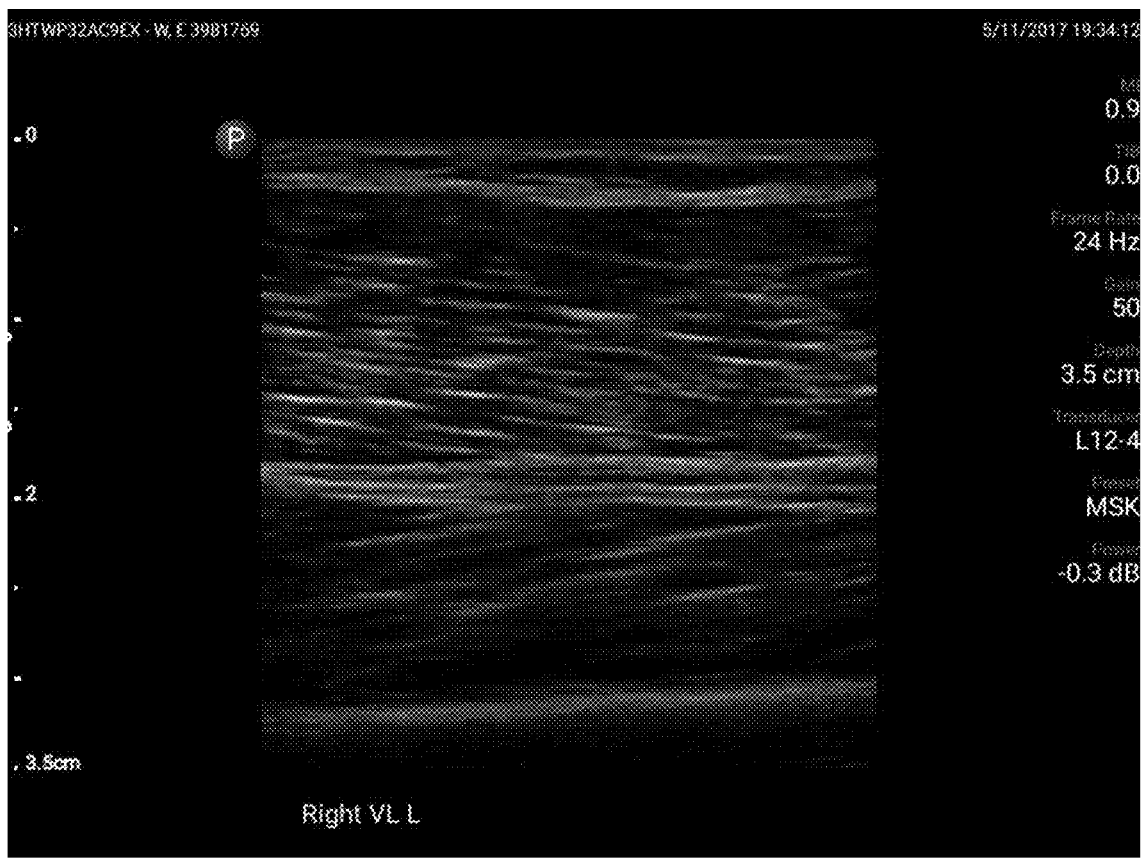
FIG. 14A depicts a conceptual illustration of an ultrasound scan of target tissues that may be used to determine pennation angle.
Figure 14B:
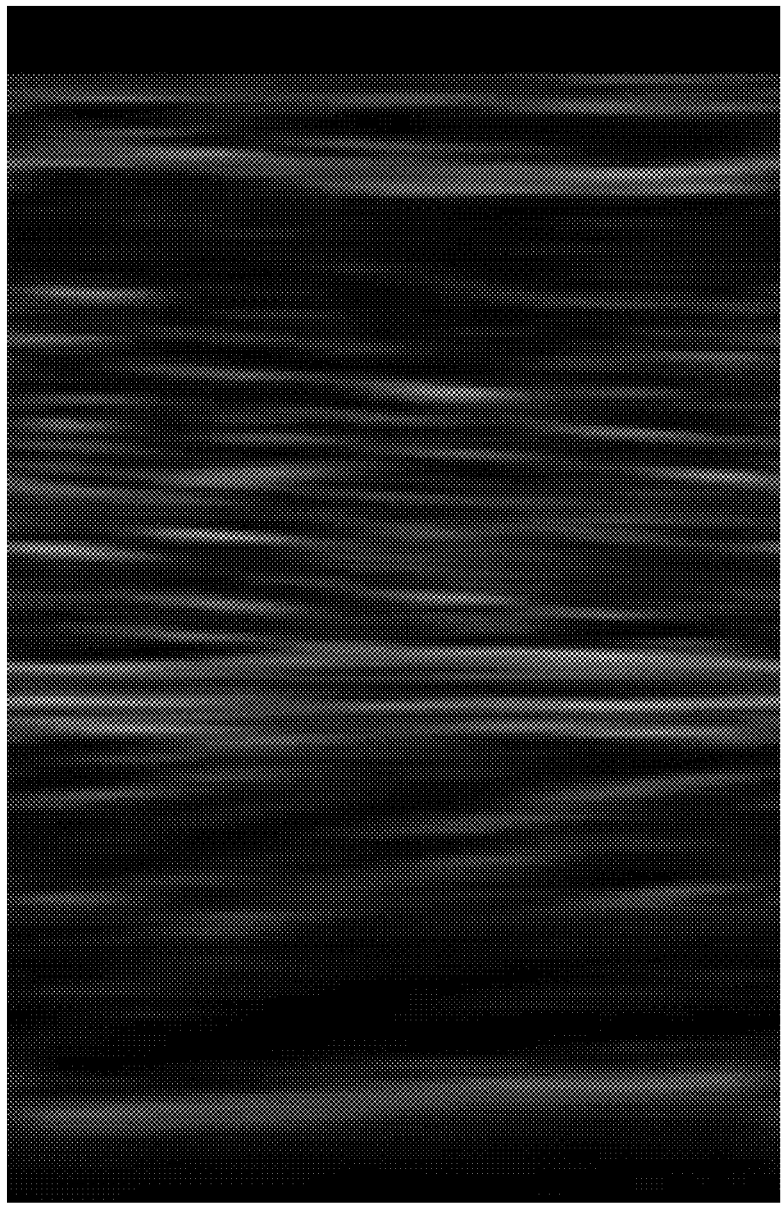
FIG. 14B depicts the ultrasound scan of FIG. 14A after performance of a blur operation.
Figure 14C:
FIG. 14C depicts the ultrasound scan of FIG. 14B after performance of a thresholding operation.
Figure 14D:
FIG. 14D depicts the ultrasound scan of FIG. 14C after performance of a morphological opening operation.
Figure 14E:
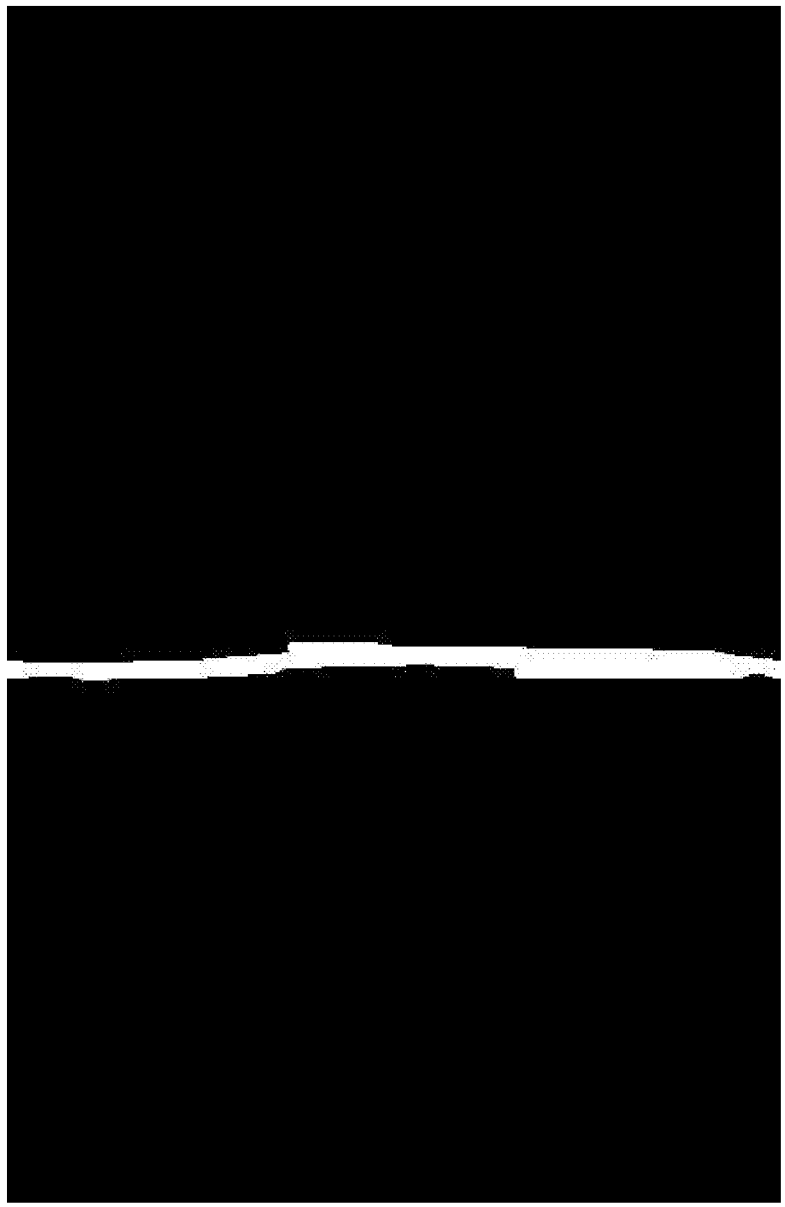
FIG. 14E depicts the ultrasound scan of FIG. 14D after features are computed to identify a reference fascia.

FIG. 14A depicts a conceptual illustration of an ultrasound scan of target tissues that may be used to determine pennation angle. The ultrasound scan of FIG. 14A may be used to find a reference tissue, such as using the operations described above with respect to 1201 of the example method 1200 and/or the example expansion 1300A, which may be performed using the SNTA 200 of FIG. 2. To find the reference tissue, a blur operation may be performed on the ultrasound scan of FIG. 14A, as shown in FIG. 14B. A thresholding operation may be performed on the blurred ultrasound scan, as shown in FIG. 14C. A morphological opening may be performed on the thresholded ultrasound scan, as shown in FIG. 14D. The morphologically opened ultrasound scan of FIG. 14D may be analyzed to compute features and find a reference fascia feature, as shown in FIG. 14E. The angle of the reference fascia feature of FIG. 14E may be measured.

Figure 14F:
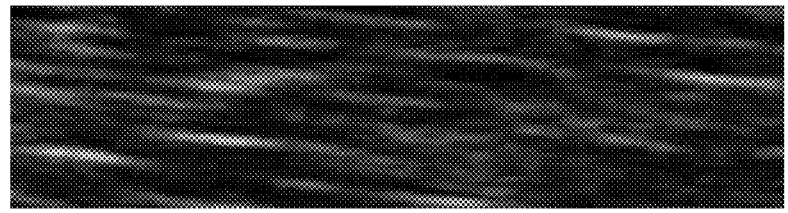
FIG. 14F depicts the ultrasound scan of FIG. 14A cropped above the reference fascia illustrated in FIG. 14E.
Figure 14G:
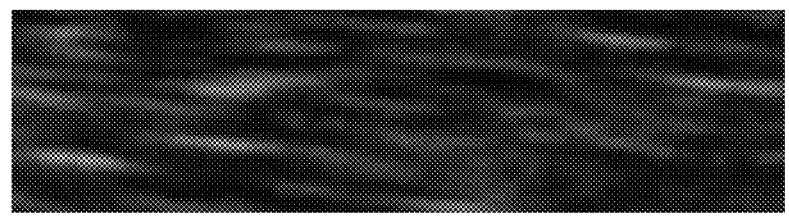
FIG. 14G depicts the ultrasound scan of FIG. 14F after performance of a blur operation.
Figure 14H:
FIG. 14H depicts the ultrasound scan of FIG. 14G after performance of a thresholding operation.
Figure 14I:
FIG. 14I depicts the ultrasound scan of FIG. 14H after features are computed.

The ultrasound scan of FIG. 14A may be used to calculate a top pennation angle, such as using the operations described above with respect to 1202 of the example method 1200 and/or the example expansion 1300B, which may be performed using the SNTA 200 of FIG. 2. To calculate the top pennation angle, the ultrasound scan of FIG. 14A may be cropped above the reference fascia feature, as shown in FIG. 14F. A blur operation may be performed on the cropped ultrasound scan, as shown in FIG. 14G. A thresholding operation may be performed on the blurred ultrasound scan, as shown in FIG. 14H. The thresholded ultrasound scan of FIG. 14H may be analyzed to compute features and filter features, as shown in FIG. 14I. The top pennation angle may be determined by subtracting the angle of the reference fascia feature determined using FIG. 14E from the computed and filtered features of FIG. 14I, such as from the highest 75% of the measured angles of the computed and filtered features of FIG. 14I.

Figure 14J:
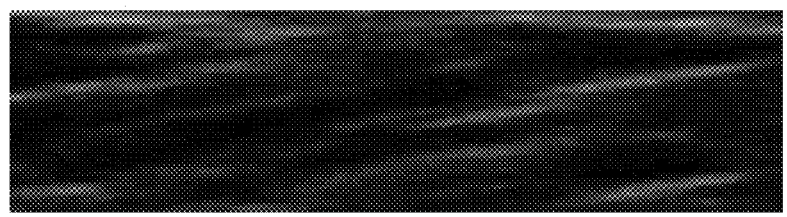
FIG. 14J depicts the ultrasound scan of FIG. 14A cropped below the reference fascia illustrated in FIG. 14E.
Figure 14K:
FIG. 14K depicts the ultrasound scan of FIG. 14J after blurring and thresholding operations are performed and features are computed.
Figure 15:
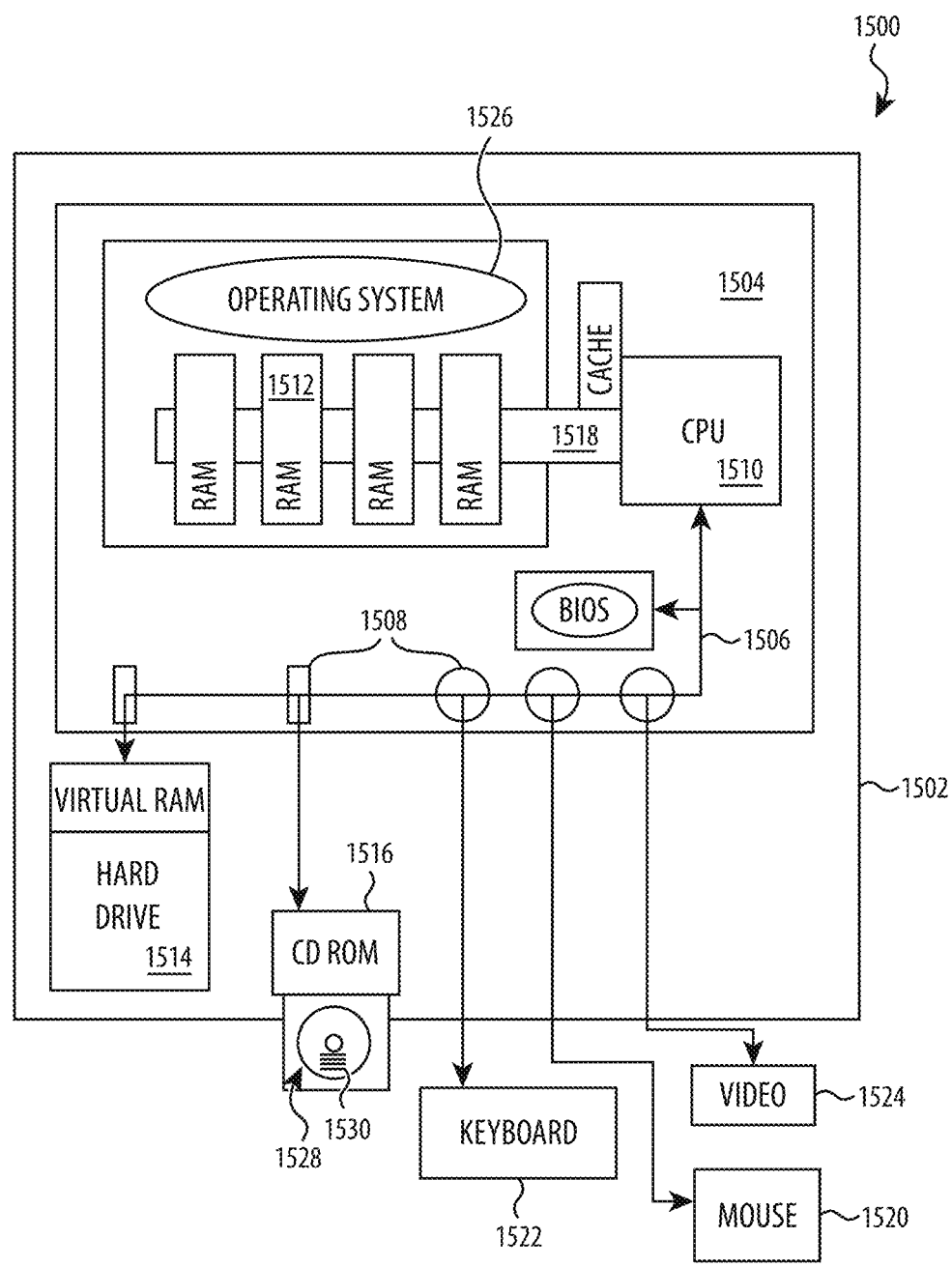
FIG. 15 depicts a block diagram of a computer system in accordance with at least one embodiment.

The ultrasound scan of FIG. 14A may be used to calculate a top pennation angle, such as using the operations described above with respect to 1203 of the example method 1200 and/or the example expansion 1300C, which may be performed using the SNTA 200 of FIG. 2. To calculate the top pennation angle, the ultrasound scan of FIG. 14A may be cropped below the reference fascia feature, as shown in FIG. 14J. The cropped ultrasound scan may then be blurred (and/or otherwise have noise introduced into it), thresholded, and analyzed to compute features and filter features, as shown in FIG. 14K. The bottom pennation angle may be determined by subtracting the angle of the reference fascia feature determined using FIG. 14E from the computed and filtered features of FIG. 14K, such as from highest 25% of the measured angles of computed and filtered features of FIG. 14K.

With respect to the above description of SNTA 200 and methods 400, 500, 1100, 1200, and expansions 1300A, 1300B, and 1300C, it is understood and appreciated that the method may be rendered in a variety of different forms of code and instruction as may be preferred for different computer systems and environments. To expand upon the initial suggestion of a processor based device such as a computer 214 shown in FIG. 2 and discussed above, FIG. 15 is a high-level block diagram of an example computer system 1500. Computer system 1500 has a case 1502, enclosing a main board 1504. The main board 1504 has a system bus 1506, connection ports 1508, a processing unit, such as Central Processing Unit (CPU) 1510 with at least one processor/microprocessor (not shown) and a memory storage device, such as main memory 1512, and optionally a solid state drive or hard drive 1514 and/or CD/DVD ROM drive 1516.

Memory bus 1518 couples main memory 1512 to CPU 1510. A system bus 1506 couples storage devices such as, but not limited to, hard drive 1514, CD/DVD ROM drive

1516 and connection ports 1508 to CPU 1510. Multiple input devices may be provided, such as for example a mouse 1520 and/or keyboard 1522. Multiple output devices may also be provided, such as for example a video display 1524 and a printer (not shown). In varying embodiments, the video display 1524 may also be a touch sensitive input device.

Computer system 1500 may be a commercially available system, such as a desktop workstation unit provided by IBM, Dell Computers, Gateway, Apple, Sun Microsystems, or other computer system provider. Computer system 1500 may also be a smart phone or tablet computer such as an iPhone or iPad provided by Apple, the HP Slate, the Augen or Archos Android tablets, the Motorola Xoom or other such device. Computer system 1500 may also be a networked computer system, wherein memory storage components such as hard drive 1514, additional CPUs 1510 and output devices such as printers are provided by physically separate computer systems commonly connected together in the network. Those skilled in the art will understand and appreciate that physical composition of components and component interconnections composing computer system 1500, and select a computer system 1700 suitable for the schedules to be established and maintained.

When computer system 1500 is activated, an operating system 1526 may load into main memory 1512 as part of the boot strap startup sequence and ready the computer system 1500 for operation. At the simplest level, and in the most general sense, the tasks of an operating system may fall into specific categories—process management, device management (including application and user interface management) and memory management.

In such a computer system 1500, the CPU 1510 may be operable to perform one or more of the methods of non-invasive determination of pennation angle and/or fascicle length as described above. Those skilled in the art will understand that a computer-readable medium 1528 on which is a computer program 1530 for non-invasive determination of pennation angle and/or fascicle length may be provided to the computer system 1500. The form of the medium 1528 and language of the program 1530 are understood to be appropriate for computer system 1500. Utilizing the memory stores, such as for example one or more hard drives 1514 and main memory 1512, the operable CPU 1510 will read the instructions provided by the computer program 1530 and operate to perform as SNTA 200 as described above.

To summarize, for at least one embodiment, a system for a non-invasive system of determining pennation angle and/or fascicle length is provided by a processing unit; a memory storage device coupled to the processing unit; the processing unit being adapted to: receive at least one ultrasound scan image of at least a portion of a skin layer as disposed above one or more additional tissue layers, the image provided by a plurality of pixels; blur (and/or otherwise introduce noise into) the pixels of the image; threshold the pixels of the image to provide a binary image having a plurality of structural elements of different sizes; morph the structural elements of the binary image to remove small structural elements and connect large structural elements; distinguish muscle fiber and tendon from remaining structural elements; and determine the pennation angle and/or fascicle length from the muscle fiber and the tendon.

Figure 16:
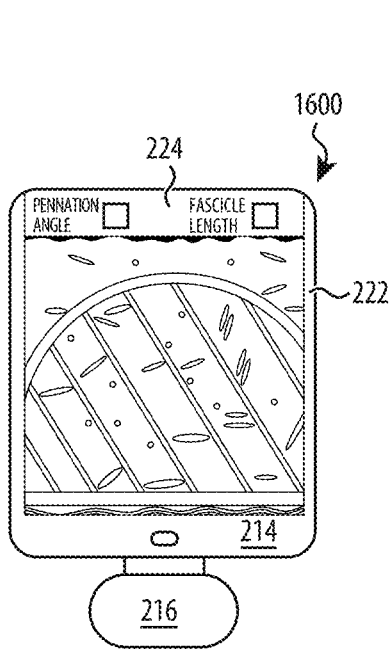
FIG. 16 depicts a conceptual illustration of a first alternative configuration for a system for non-invasive tissue evaluation that may be used to determine human pennation angle and/or fascicle length in accordance with at least one embodiment.

With respect to the various forms of the processor based device, such as the computer 214, further discussed and described as computer system 1500, FIGS. 16-21 present alternative embodiments for the structural arrangement of components composing SNTA 200. More specifically, for alternative SNTA 1600 as shown in FIG. 16, the ultrasound transducer 216 is coupled directly to the computer 214, such that SNTA 1600 is itself disposed adjacent to the target tissue 208 (not shown).

Figure 17:
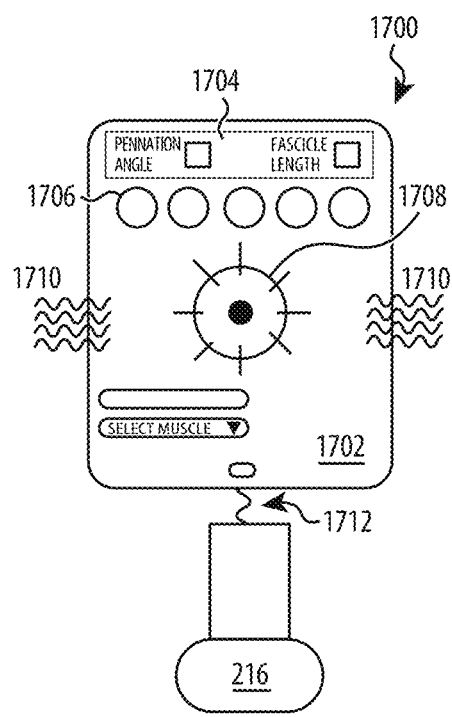
FIG. 17 depicts a conceptual illustration of a second alternative configuration for a system for non-invasive tissue evaluation that may be used to determine human pennation angle and/or fascicle length in accordance with at least one embodiment.

For alternative SNTA 1700 shown as FIG. 17, a dedicated processor based device such as a customized computer 1702 is provided, as opposed to adapting a pre-existing smart phone, tablet computer or other computer system. For SNTA 1700, the display 222 of SNTA 1700 is not shown so as to illustrate that alternative output devices such as an indicator 1704, lights 1706, speaker 1708, vibrator 1710 and/or combinations thereof can provide an operator with an indication of the non-invasively determined pennation angle and/or fascicle length. As with SNTA 1600, the ultrasound transducer 216 may be directly coupled to the customized computer 1702, or tethered by a communications link 1712—wireless or wired as shown.

Further, for yet other embodiments, the computer program 218 executable to adapt a computer 214 may be provided directly by enhanced ultrasound transducer 1800. More specifically, the computer program 218 may be incorporated as part of the circuit structure 1802 of enhanced ultrasound transducer 1800 such that upon connection to the computer 214, SNTA 200 is provided.

Figure 18:
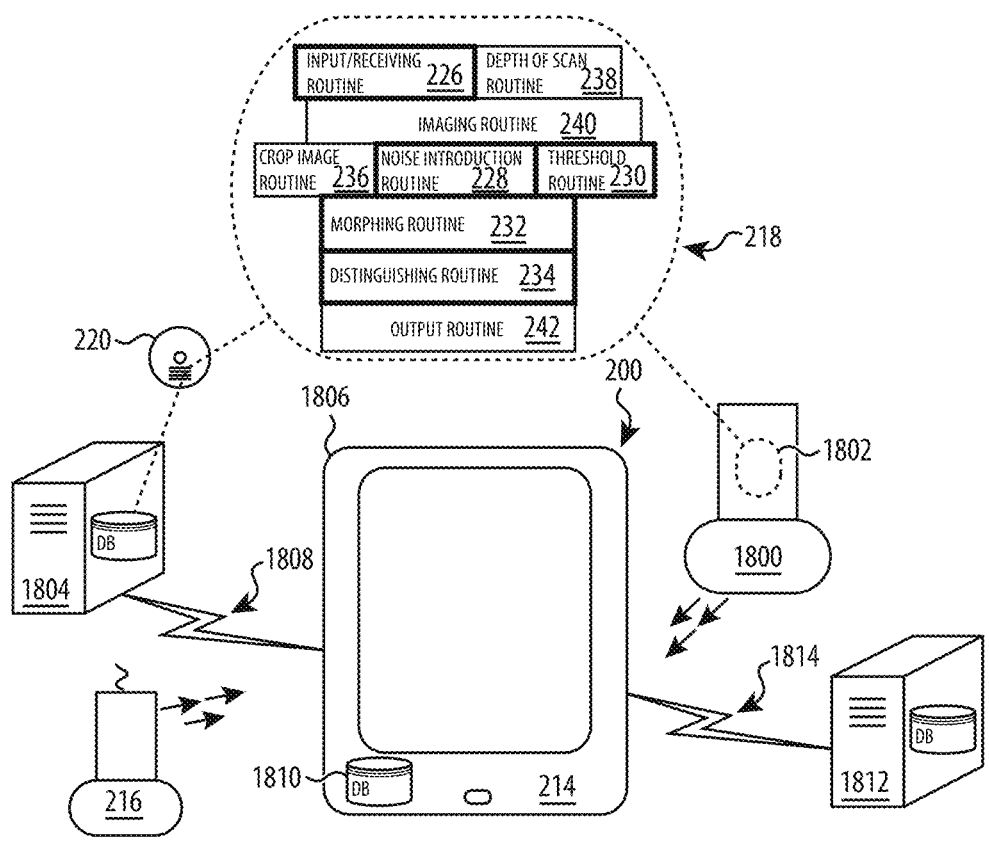
FIG. 18 depicts a conceptual illustration of a third alternative configuration for a system for non-invasive tissue evaluation that may be used to determine human pennation angle and/or fascicle length in accordance with at least one embodiment.

As suggested above with respect to FIG. 2 and as shown in shown as FIG. 18, the computer program 218 may also be provided by a non-portable media such as a disc 220 to a third party computer, such as computer 1804, providing an application platform such as, but not limited to, the Apple App Store. A user can then connect his or her computer 214, such as tablet computer 1806 to the third party computer 1804 by a network 1808 (wired or wireless) or other communication channel and obtain computer program 218 so as to adapt his or her computer 1806 to perform as SNTA 200 when a scan of a target muscle is provided.

In varying embodiments, this scan may be provided by coupling computer 1806 to ultrasound transducer 216 operated as described above, receiving a scan of a target muscle from internal storage 1810, or receiving a scan of a target muscle from another computer system 1812 via wired or wireless network 1814, or other appropriate communication channel.

Figure 19:
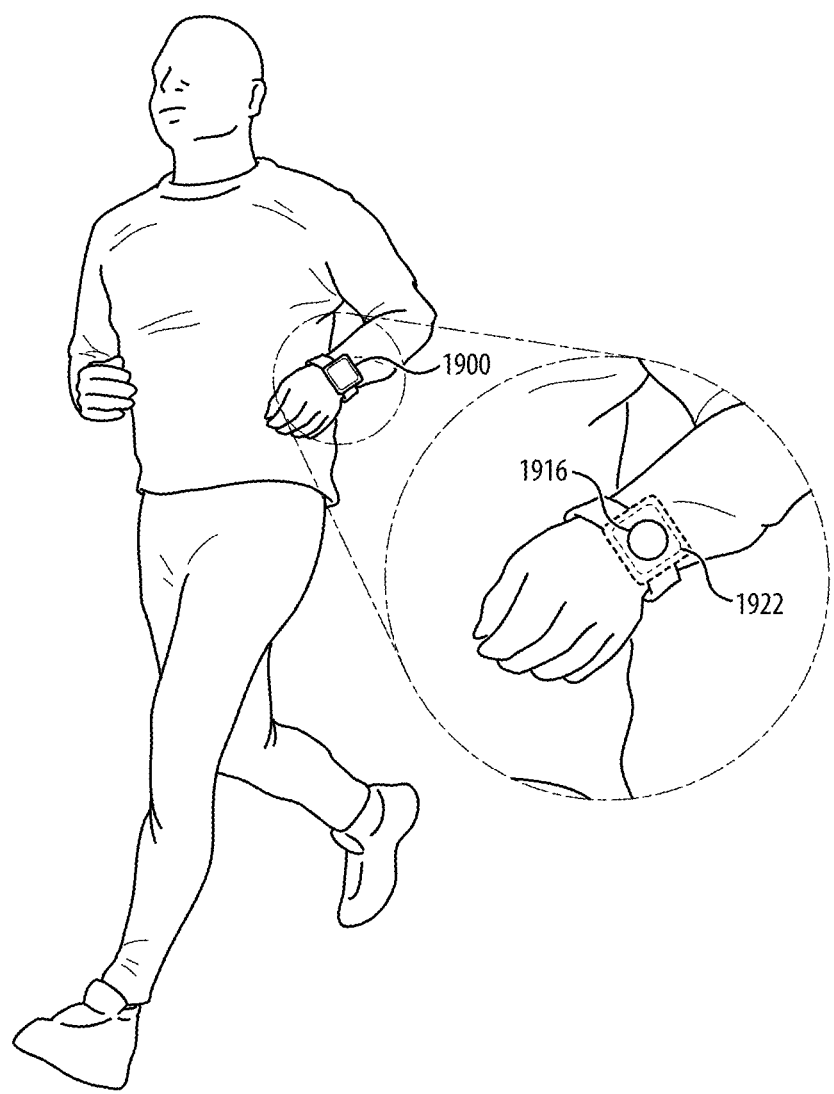
FIG. 19 depicts a conceptual illustration of a fourth alternative configuration for a system for non-invasive tissue evaluation that may be used to determine human pennation angle and/or fascicle length in accordance with at least one embodiment.

As shown in FIG. 19, in some embodiments, the SNTA 1900 may be a wearable device, such as a smart watch or other device operable to couple around a user's body part. The SNTA 1900 may include a transducer 1916 positioned adjacent the user in order to obtain scans and/or other data at a variety of different times, such as during a user's workout. The SNTA 1900 may also include a display 1922 for providing real time and/or other analysis information to the user.

Figure 20:
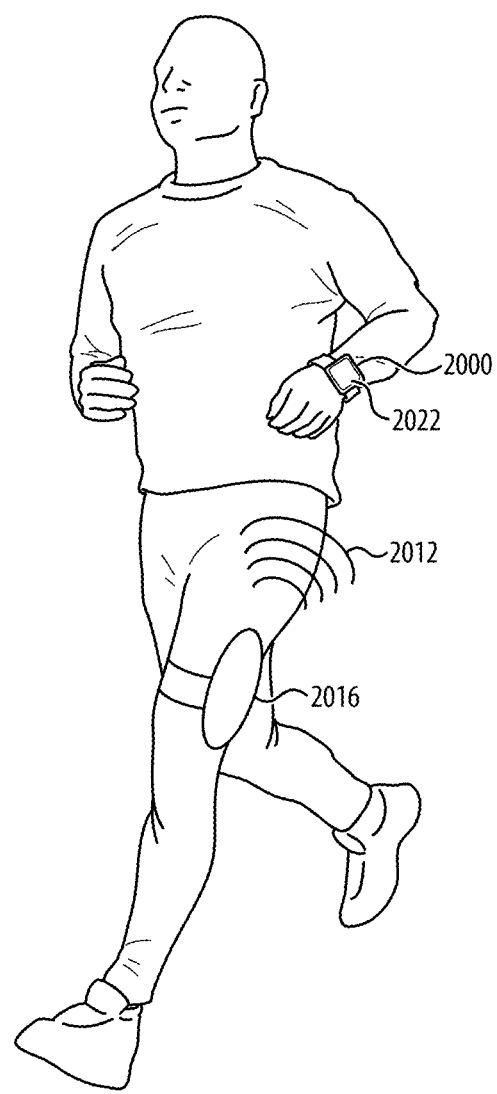
FIG. 20 depicts a conceptual illustration of a fifth alternative configuration for a system for non-invasive determination of human pennation angle and/or fascicle length in accordance with at least one embodiment.

As shown in FIG. 20, in other embodiments, a wearable SNTA 2000 may be used with a separately wearable transducer 2016. In this way, the SNTA 2000 may be coupled around one body part while the transducer 2016 obtains one or more scans related to tissues located in another body part. The SNTA 2000 may receive data regarding such scans from the transducer 2016, such as wirelessly 2012, and provide real time and/or other analysis information to the user via a display 2022.

Figure 21:
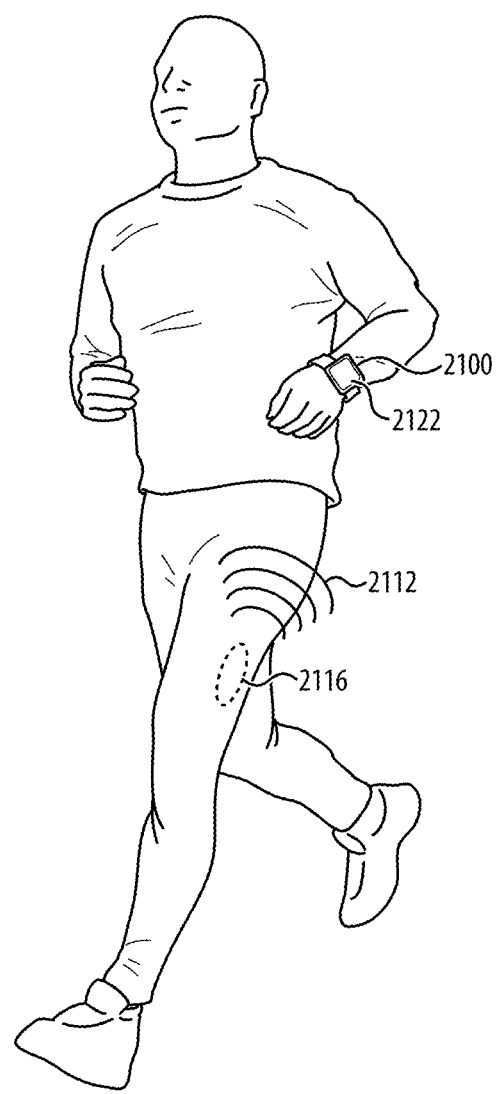
FIG. 21 depicts a conceptual illustration of a sixth alternative configuration for a system for non-invasive determination of human pennation angle and/or fascicle length in accordance with at least one embodiment.

As shown in FIG. 21, in still other embodiments, a wearable SNTA 2100 may be used with a transducer implant 2116 located inside the user's body. In this way, the SNTA 2100 may obtain one or more scans related to tissues located in the body without requiring attachment and positioning of a transducer for use. The SNTA 2100 may receive data regarding such scans from the transducer implant 2116, such as wirelessly 2112, and provide real time and/or other analysis information to the user via a display 2122.

To summarize, for at least one embodiment, the present disclosure is provided upon a non-transitory machine readable medium on which is stored a computer program including instructions to adapt a computer system having a processor to permit non-invasive determination of human pennation angle and/or fascicle length. This computer program includes computer executable instructions to provide a receiving routine operatively associated with an input device for receiving at least one ultrasound scan image of at least a portion of a skin layer as disposed above one or more additional tissue layers, the image provided by a plurality of pixels; a blurring and/or other noise introduction routine for horizontally blurring and/or otherwise introducing noise into the pixels of the image; a thresholding routine for thresholding the pixels of the image to provide a binary image having a plurality of structural elements of different sizes; a morphing routine for morphing the structural elements of the binary image to remove small structural elements and connect large structural elements; and a distinguishing routine for distinguishing muscle fiber and tendon from remaining structural elements and determining the pennation angle and/or fascicle length from the muscle fiber and tendon.

As discussed above and illustrated in the accompanying figures, the present disclosure relates to non-invasive determination of human pennation angle and/or fascicle length. An ultrasound scan image is processed to facilitate distinguishing of muscle fiber and tendon. The processed ultrasound scan image is then analyzed. The pennation angle and/or fascicle length is determined based on the analysis.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall therebetween.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic device that determines a pennation angle and returns advice to a user, comprising:
   at least one non-transitory storage medium that stores instructions; and at least one processing unit that executes the instructions to:
   process an ultrasound scan image to generate a processed image in order to simplify distinguishing a target muscle tissue in the processed image, wherein the processing of the ultrasound scan image comprises:
      introducing noise;
      thresholding;
      removing a first element;
      joining second elements that are larger than the first element; and
      cropping the ultrasound scan image to focus on the target muscle tissue;
   distinguish the target muscle tissue in the processed image;
   use the processed image to determine the pennation angle of the target muscle tissue, thereby providing a determined pennation angle;
   determine whether the determined pennation angle is less than or greater than a desired pennation angle; and
   return the advice to the user based on the pennation angle being less than or greater than the desired pennation angle,
   wherein the advice is related to increasing or decreasing the pennation angle to become more like the desired pennation angle.

2. The electronic device of claim 1, wherein the at least one processing unit determines the pennation angle by:
   finding features in the processed image;
   measuring angles of the features; and
   subtracting a portion of the measured angles from a reference fascia angle of a reference fascia wherein the reference fascia, the features, and the target muscle tissue are not identical.

3. The electronic device of claim 1, wherein the advice is regarding food.

4. The electronic device of claim 1, wherein the advice includes increased or decreased protein.

5. The electronic device of claim 1, wherein the cropping crops a portion of the ultrasound scan image below the target muscle tissue.

6. The electronic device of claim 1, wherein the advice includes increased or decreased carbohydrates.

7. The electronic device of claim 1, wherein the advice includes performance of specific exercises.

8. A non-invasive method of determining a pennation angle and returning advice to a user, comprising:

processing a scan image to generate a processed image in order to simplify distinguishing a target muscle tissue in the processed image, wherein the processing of the scan image comprises:
introducing noise:
thresholding:
removing a first element:
joining second elements that are larger than the first element; and
cropping the ultrasound scan image to focus on the target muscle tissue:
distinguishing the target muscle tissue in the processed image;
determining the pennation angle of the target muscle tissue by analyzing the processed image, thereby providing a determined pennation angle;
determining whether the determined pennation angle is less than or greater than a desired pennation angle; and
returning the advice to the user based on the pennation angle being less than or greater than the desired pennation angle,
wherein the advice is related to increasing or decreasing the pennation angle to become more like the desired pennation angle.

9. The method of claim 8, further comprising reporting the determined pennation angle.

10. The method of claim 8, wherein the desired pennation angle is a previously determined pennation angle.

11. The method of claim 8, wherein the desired pennation angle is a pennate measurement of another user.

12. The method of claim 8, wherein the advice is related to changes to exercise.

13. The method of claim 8, further comprising evaluating muscle health of the user.

14. The method of claim 8, wherein the desired pennation angle is a previously determined pennation angle of another muscle of a same type.

15. A computer program product storing instructions executable to perform a method of determining a pennation angle and returning advice to a user, comprising:
a first set of instructions, stored in at least one non-transitory computer readable medium, executable by at least one processing unit to process an ultrasound image to generate a processed image in order to simplify distinguishing a target muscle tissue in the processed image, wherein the processing of the ultrasound image comprises:
introducing noise:
thresholding:
removing a first element:
joining second elements that are larger than the first element; and
cropping the ultrasound scan image to focus on the target muscle tissue;
a second set of instructions, stored in the at least one non-transitory computer readable medium, executable by the at least one processing unit to: distinguish the target muscle tissue in the processed image;
a third set of instructions, stored in the at least one non-transitory computer readable medium, executable by the at least one processing unit to distinguish muscle fiber of the target muscle tissue from remaining structural elements;
a fourth set of instructions, stored in the at least one non-transitory computer readable medium, executable by the at least one processing unit to determine the pennation angle of the target muscle tissue, thereby providing a determined pennation angle;
a fifth set of instructions, stored in the at least one non-transitory computer readable medium, executable by the at least one processing unit to determine whether the determined pennation angle is less than or greater than a desired pennation angle; and
a sixth set of instructions, stored in the at least one non-transitory computer readable medium, executable by the at least one processing unit to return the advice to the user based on the pennation angle being less than or greater than the desired pennation angle,
wherein the advice is related to increasing or decreasing the pennation angle to become more like the desired pennation angle.

16. The computer program product of claim 15, further comprising a seventh set of instructions, stored in the at least one non-transitory computer readable medium, executable by the at least one processing unit to determine a fascicle length.

17. The computer program product of claim 16, further comprising an eighth set of instructions, stored in the at least one non-transitory computer readable medium, executable by the at least one processing unit to report the fascicle length.

18. The computer program product of claim 16, further comprising an eighth set of instructions, stored in the at least one non-transitory computer readable medium, executable by the at least one processing unit to compare the fascicle length to a desired fascicle length.

19. The computer program product of claim 16, further comprising an eighth set of instructions, stored in the at least one non-transitory computer readable medium, executable by the at least one processing unit to provide output related to altering the fascicle length.

20. The computer program product of claim 16, further comprising an eighth set of instructions, stored in the at least one non-transitory computer readable medium, executable by the at least one processing unit to evaluate fitness of the user based on the fascicle length.

* * * * *